United States Patent [19]

Hall et al.

[11] Patent Number: 4,458,093
[45] Date of Patent: Jul. 3, 1984

[54] HEXADIENOYL CYCLOHEXENE DERIVATIVE

[75] Inventors: John B. Hall, Rumson; Joseph A. McGhie, Montclair; Manfred H. Vock, Locust, all of N.J.

[73] Assignee: International Flavors & Fragrances Inc., New York, N.Y.

[21] Appl. No.: 496,801

[22] Filed: May 20, 1983

[51] Int. Cl.³ .......................................... C07C 49/557
[52] U.S. Cl. ............................... 568/378; 252/522 R; 426/534; 426/650; 560/126; 568/346
[58] Field of Search ........................................ 568/378

[56] References Cited

U.S. PATENT DOCUMENTS 3,923,896 12/1975 Schulte-Elte ........................ 564/253
4,202,994 5/1980 Trenkle et al. ..................... 568/378
4,324,704 4/1982 Trenkle et al. ..................... 568/378
4,334,098 6/1982 Mookheijee et al. ............... 568/341

FOREIGN PATENT DOCUMENTS 566112 9/1975 Switzerland .

OTHER PUBLICATIONS

*Chemical Abstracts,* vol. 3, p. 167, (1909), Wahl et al.

Primary Examiner—Natalie Trousof
Assistant Examiner—Patricia M. Scott
Attorney, Agent, or Firm—Arthur L. Liberman

[57] ABSTRACT

Described is the hexadienoyl cyclohexene derivative defined according to the structure:

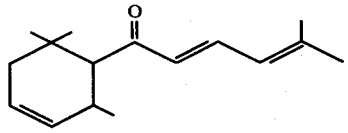

which may either be in the form of a mixture of Z, Z; E, E; Z, E or E, Z isomers or the individual isomers themselves having the structures:

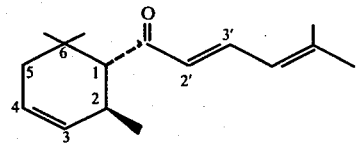

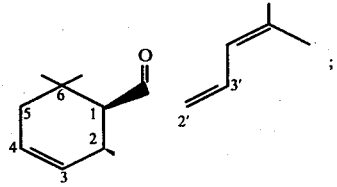

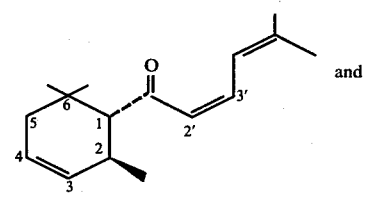

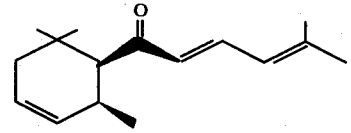

a process for preparing same, intermediates useful in said process defined according to the structure:

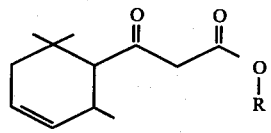

wherein R represents ethyl or methyl and organoleptic uses of the hexadienoyl cyclohexene derivatives in augmenting or enhancing the aroma or taste of consumable materials including perfume compositions, colognes and perfumed articles (e.g. solid or liquid anionic, cationic, nonionic or zwitterionic detergents, hair preparations, fabric softeners, fabric softener articles, cosmetic powders and perfumed polymers); foodstuffs, chewing gums, medicinal products, toothpastes and chewing tobaccos; smoking tobaccos and smoking tobacco articles.

1 Claim, 12 Drawing Figures

GLC PROFILE FOR EXAMPLE II. CRUDE

GLC PROFILE FOR EXAMPLE I. CRUDE

GLC PROFILE FOR FRACTION 1 OF EXAMPLE II. FIRST DISTILLATION

GLC PROFILE FOR FRACTION 2 OF EXAMPLE II. FIRST DISTILLATION

GLC PROFILE FOR FRACTION 5 OF EXAMPLE II. REDISTILLATION

GLC PROFILE FOR FRACTION 4 OF EXAMPLE II. REDISTILLATION

GLC PROFILE FOR FRACTION 7 OF EXAMPLE II. REDISTILLATION

GLC PROFILE FOR FRACTION 6 OF EXAMPLE II. REDISTILLATION

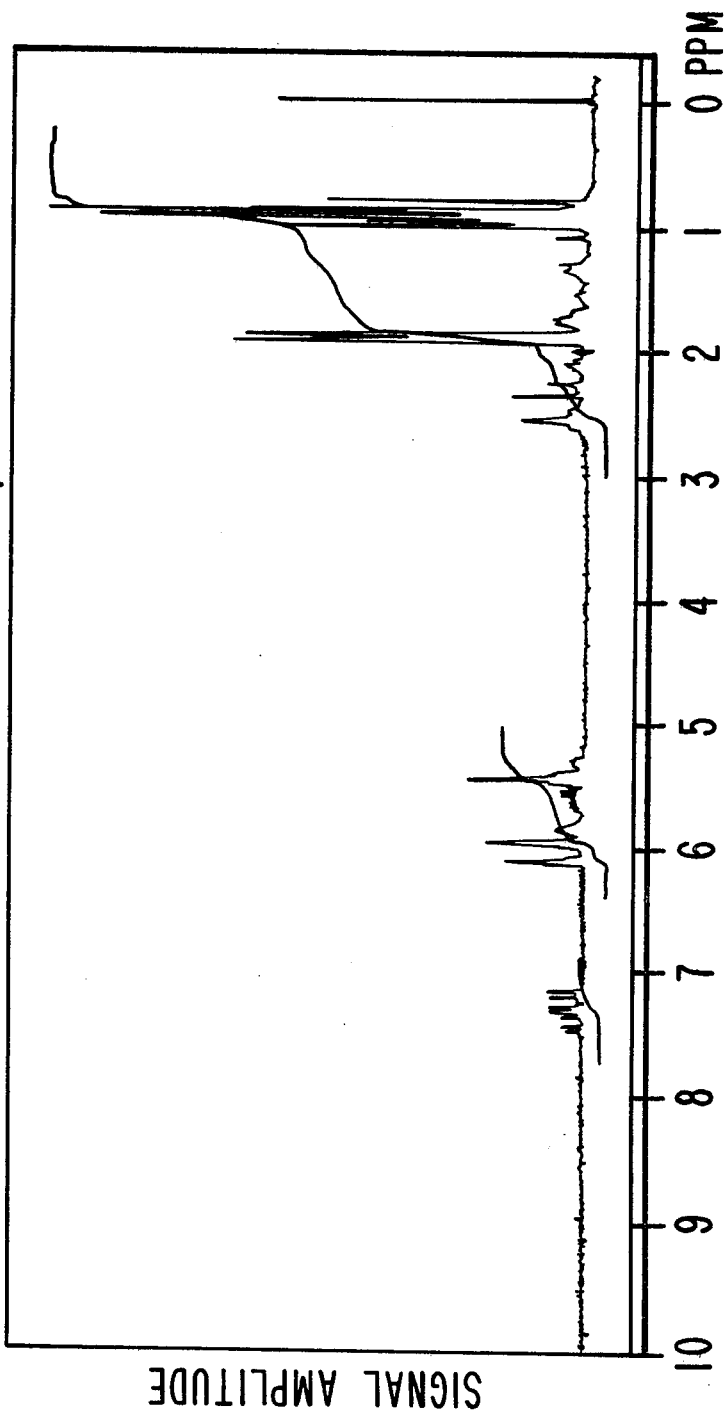

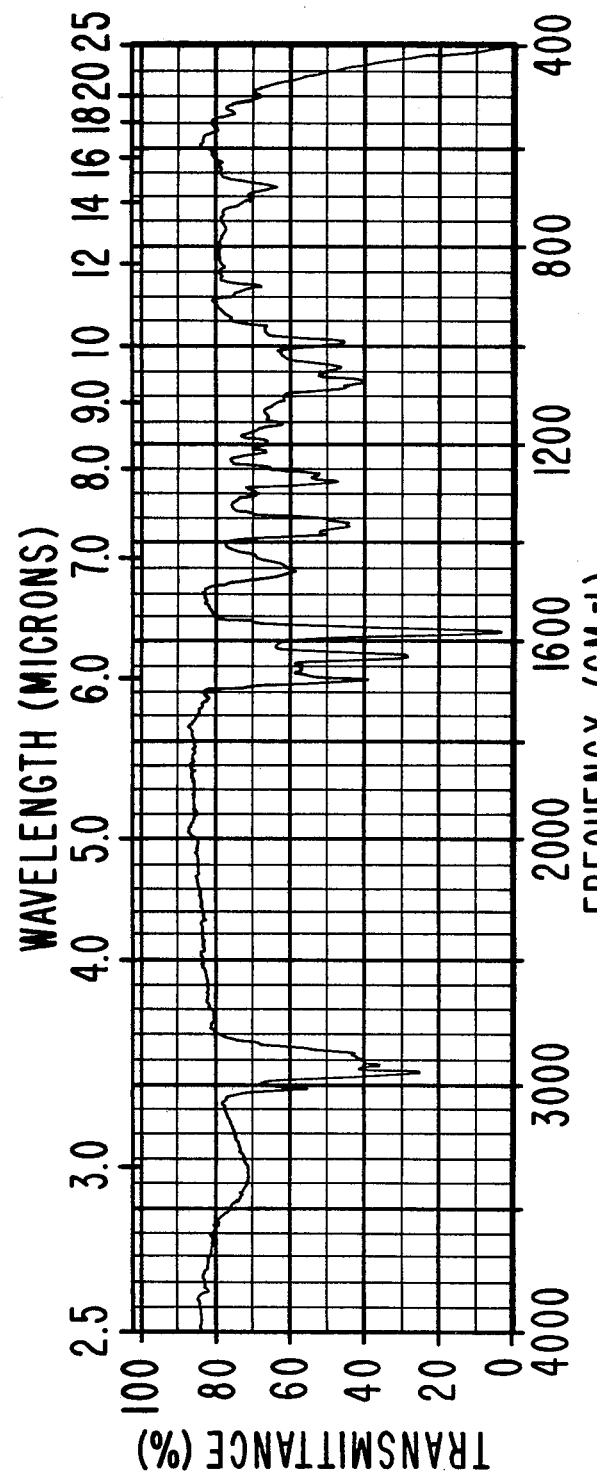

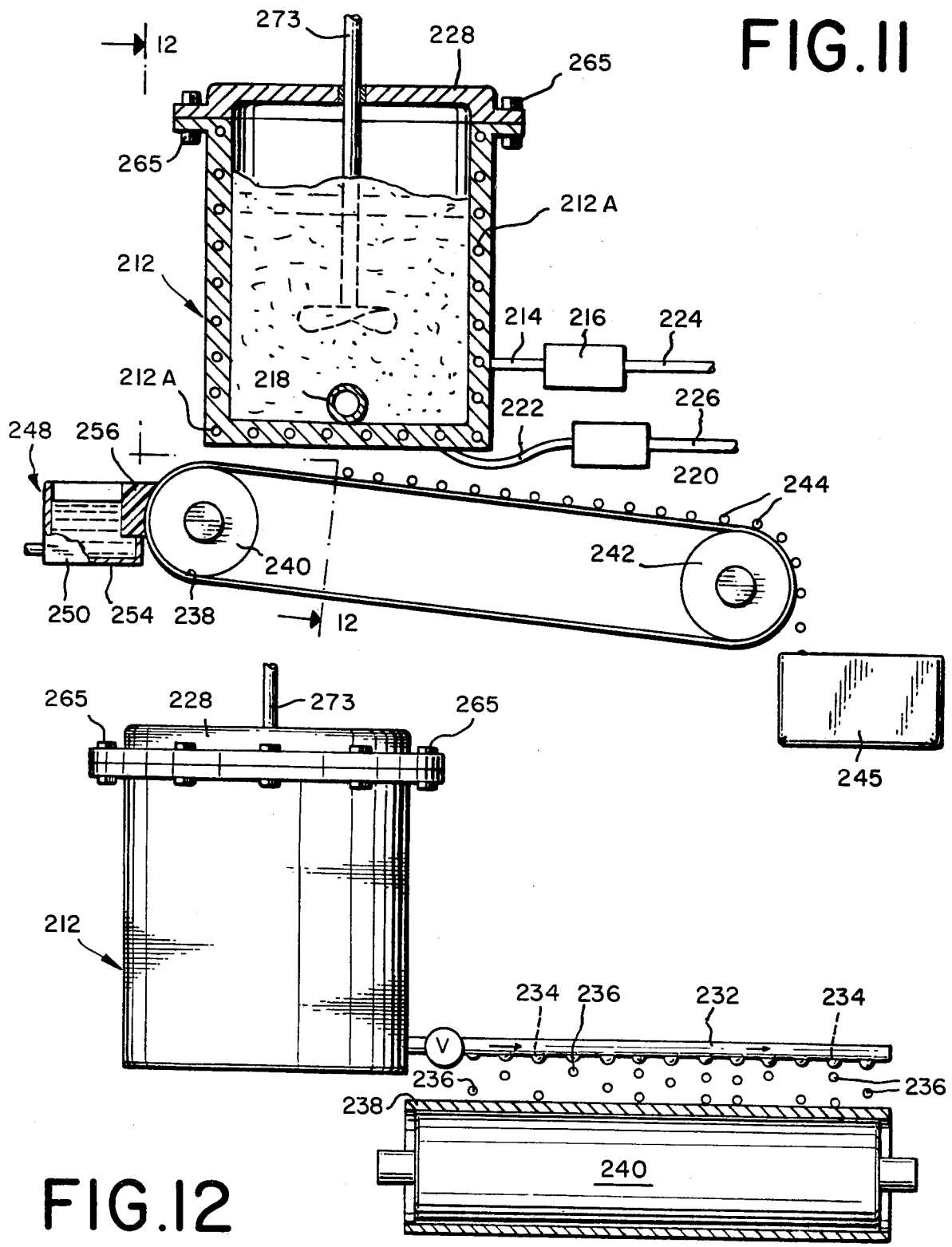

HEXADIENOYL CYCLOHEXENE DERIVATIVE

BACKGROUND OF THE INVENTION

The instant invention relates to hexadienoyl cyclohexene derivatives generically defined according to the structure:

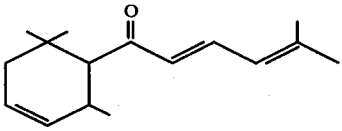

processes for preparing said hexadienoyl cyclohexene derivatives, and organoleptic uses of said hexadienoyl cyclohexene derivatives in augmenting or enhancing the aroma or taste of consumable materials.

In the perfumery art there is considerable need for substituents having floral, rosey, honey, woody and raspberry aroma nuances.

Floral, hay-like, sweet and fruity notes are desirable in smoking tobacco flavoring compositions and substitute smoking tobacco flavoring compositions.

Minty, citrus, lime, raspberry, floral, and rosey aroma and taste nuances with fresh, cooling nuances are highly desirable in flavoring compositions for foodstuffs, chewing gums, medicinal products, toothpastes and chewing tobaccos.

A limited number of materials which give rise to the foregoing properties are available from natural sources. The natural materials are subject to wide variations in quality, are expensive and are often in critically short supply.

In addition, there is a continuing search for food flavor compositions which can vary, fortify, modify, enhance, augment or otherwise improve the flavor and/or aroma of foodstuffs, medicinal products, toothpastes, chewing gums and chewing tobaccos. To be satisfactory, such compositions would be stable, non-toxic and blendable with other ingredients to provide their own unique flavor and aroma nuances without detracting from the co-ingredients. Preferably such compositions should be naturally occurring or be present in the natural foodstuff so that their ingestible safety can be readily recognized. These materials should be capable of being synthesized in a simple and economical manner. The need for safe flavors particularly in the lime, citrus, tropical fruit, and mint areas is well known, particularly in the oral hygiene areas. More specifically, there is a need for the development of non-toxic materials which can replace natural materials not readily available having minty, citrus, lime, raspberry, floral and rosey aroma and taste nuances with fresh, cooling nuances.

The instant invention provides the foregoing which the prior art has heretofore failed to provide. Furthermore, nothing in the prior art shows the unexpected, unobvious and advantageous value of the genus of compounds defined according to the structure:

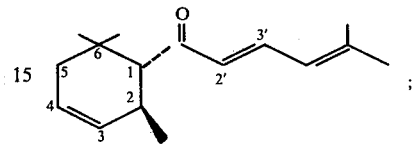

and particularly the isomers thereof having the structures:

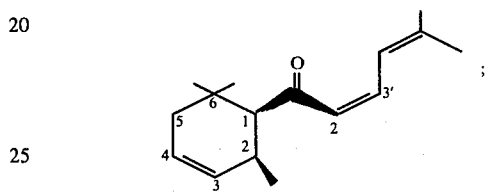

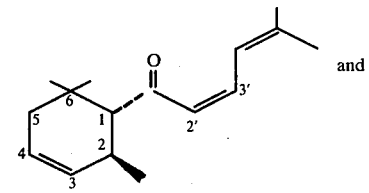

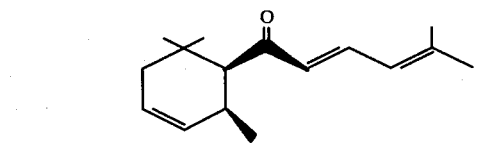

and

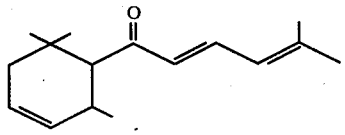

U.S. Pat. No. 4,334,098 issued on June 8, 1982 discloses the use of the compound trans,transdelta damascone having the structure:

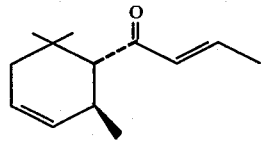

for its organoleptic properties. The compound having the structure:

and its isomers individually have properties which are unexpected, unobvious and advantageous over the properties of the trans,trans-delta-damascone defined according to the structure:

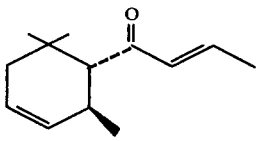

Hexadienoyl cyclohexenes having trimethyl substitution on the cyclohexene ring are known for use in augmenting or enhancing the organoleptic properties of consumable materials in the prior art. Thus, Arctander "Perfume and Flavor Chemicals (Aroma Chemicals)", Volume I published in 1969 discloses at monograph 86 the compound having the structure:

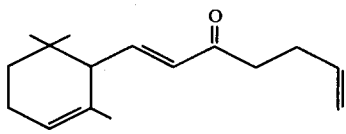

(allyl ionone) thusly:

86: ALLYL IONONE alpha-Allyl ionone (Allyl-alpha-ionone).
"Hexalon" (I.F. & F. Inc.).
"Cetone V." (Givaudan).
"Polyone" (Firmenich).
Allyl cyclocitrylidene acetone.
1-(2,6,6-Trimethyl-2-cyclohexene-1-yl)-1,6-heptadien-3-one.

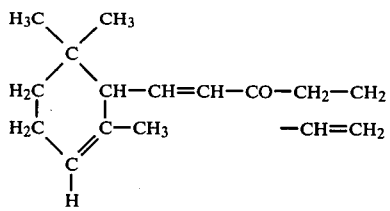

$C_{16}H_{24}O = 232.35$

Colorless or very pale yellowish oily liquid. B.P. about 265° C. Sp. Gr. 0.930.
Oily-sweet, slightly flowery, but also fruity, woody and bark-like green odor of considerable tenacity. According to the identity of the manufacturer, the odor characteristics of this chemical may vary from mild-oily fruity-woody to peculiar fishy (amine-like), woody, cod-liver oil-like, etc. The odor changes also with age, particularly under poor storage condition. This is one of the main drawbacks of the title chemical.
  Ketone content of commercial grades: 88 to 93%.
  Insoluble in water, soluble in alcohol and perfume and flavor materials, poorly soluble in Propylene glycol.
  Useful in perfume compositions as a modifier for Ionones and Methylionones, in modern-aldehydic creations, in perfumes with fruity-aldehydic topnotes, in combinations with Vetiver or woody-floral perfume materials, etc. "Cetone V." is probably the most fruity of all commercial Allyl ionones.
  Used in flavors-traces-for imitation Raspberry and Pineapple.
  Produced from Citral by condensation with Allyl acetone, followed by cyclization.
  G.R.A.S. F.E.M.A. No. 2033.
  3-171; 31-96; 86-5; 106-94; 155-92; 89-389; 156-203;

and further discloses the organoleptic properties of beta-euionone at monograph 1377, beta-euionone having the structure:

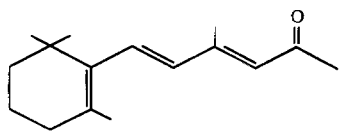

thusly:

1377: beta-EUIONONE

2-Methyl-4-(1,1,3-trimethyl-2'-cyclohexen-2'-yl)-butadiene methylketone.
4-Methyl-6-(1,1,3-trimethyl-2'-cyclohexen-2'-yl)-3,5-hexadien-2-one.

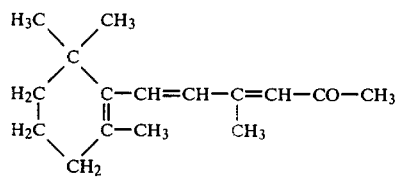

$C_{16}H_{24}O = 232.37$

Almost colorless or pale straw-colored oily liquid.
Semi-sweet, woody and slightly fruity, warm odor of good tenacity and some resemblance to beta-Ionone, but more sweet, less woody than that material.
This ketone has been suggested for use in perfume compositions as being superior to beta-Ionone with respect to overall odor performance and versatility in use.
However, the manufacture of this material is somewhat more costly than that of the Ionones, at least as long as no one can set up a truly large scale production of this chemical. There is also some doubt that it can replace, let alone outperform, any of the common Ionones as far as odor quality is concerned.
Prod.: from Citral and iso-Propylidene acetone by condensation followed by cyclization.
31-95; 86-51; 86-78;
See also: Ianthone.

Neither allyl ionone nor beta-euionone have properties even remotely similar to the organoleptic properties of the compound having the structure:

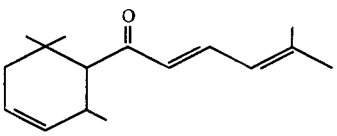

or its individual isomers having the structures:

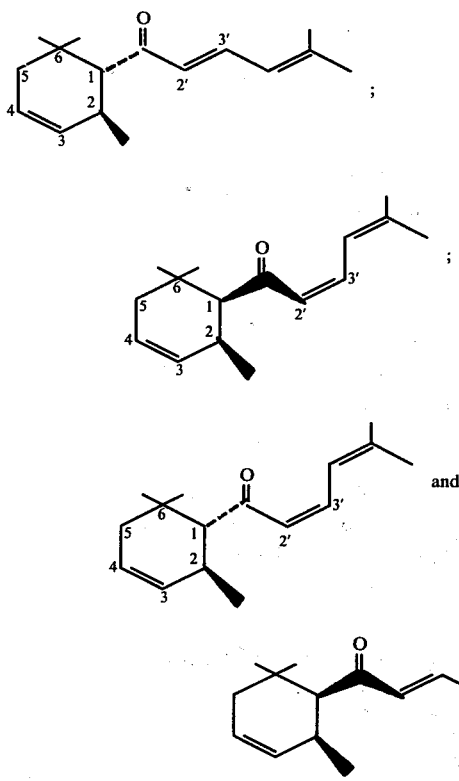

Nothing in the prior art discloses the efficient, economically method for synthesizing the compounds having the structure:

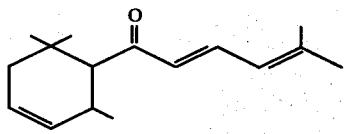

through the intermediate genus having the structure:

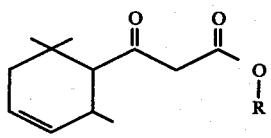

wherein R represents methyl or ethyl according to the reaction sequence:

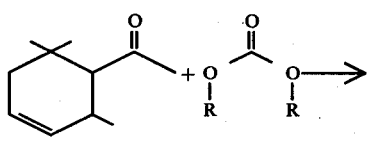

and

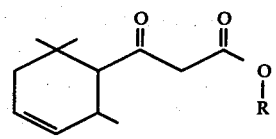

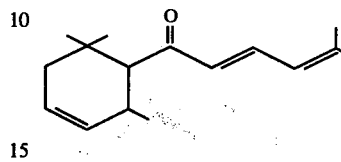

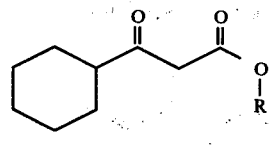

However, Chem. Abstracts, Volume 3, page 167 at line 37 (abstracting Wahl and Mayer, Bull. Soc. Chim. [4], 3, 957-63 (September, October 1906) discloses the synthesis of the compound having the structure:

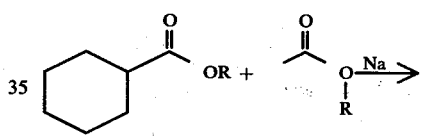

wherein R is methyl or ethyl according to the reaction:

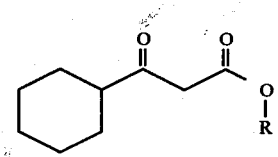

The reaction set forth above is different in kind rather than degree from the reaction of the instant invention, to wit:

wherein R represents methyl or ethyl.

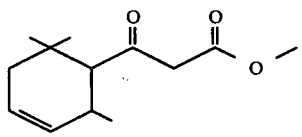

which include the isomers defined according to the structures:

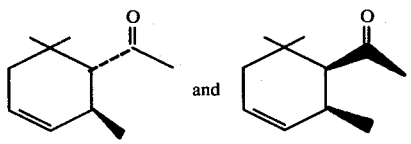

("Z") and "E" isomers).

Figure 2:
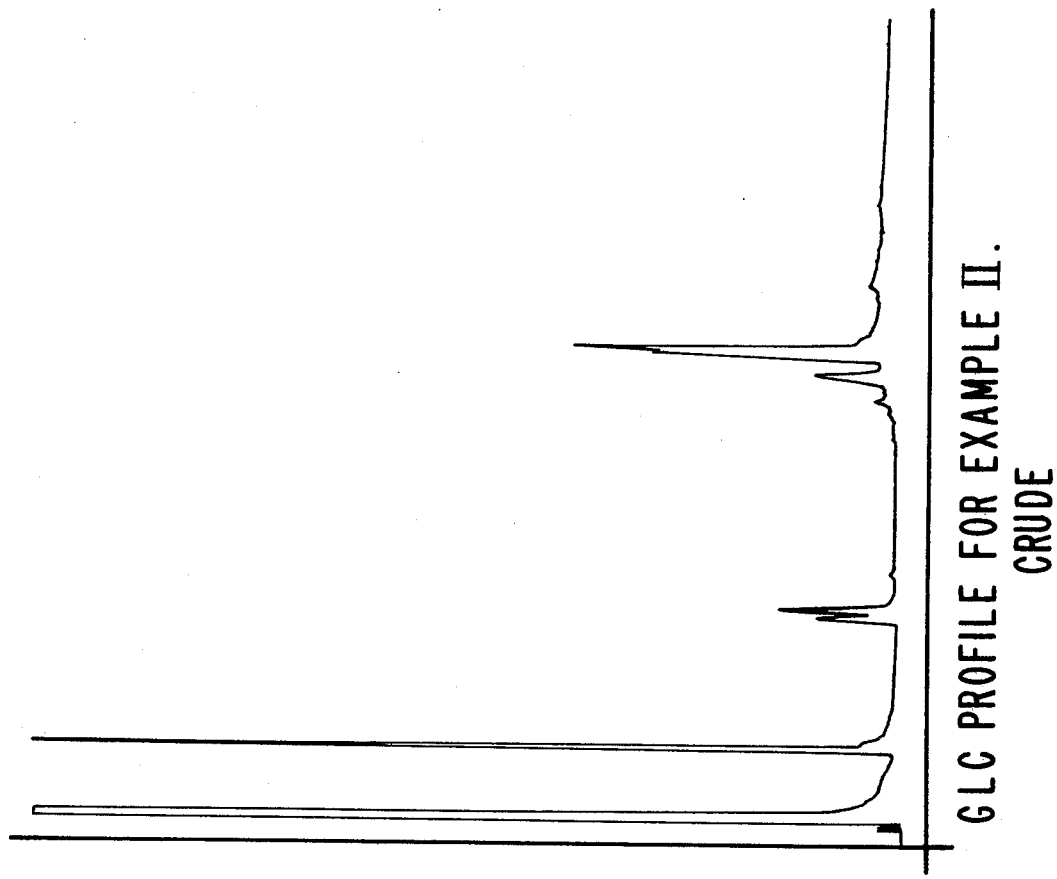

FIG. 2 is the GLC profile for the crude reaction product of Example II containing the compounds defined according to the structure:

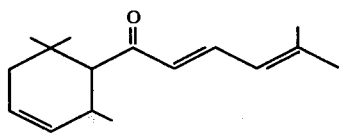

which include the isomers having the structures:

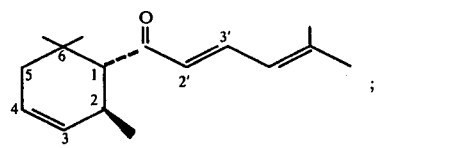

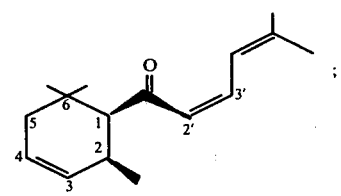

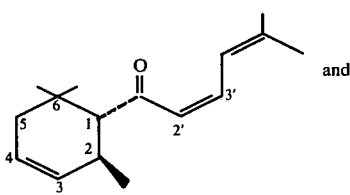

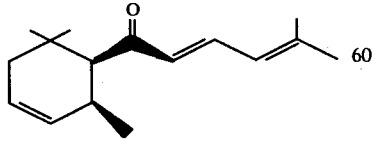

Figure 3:
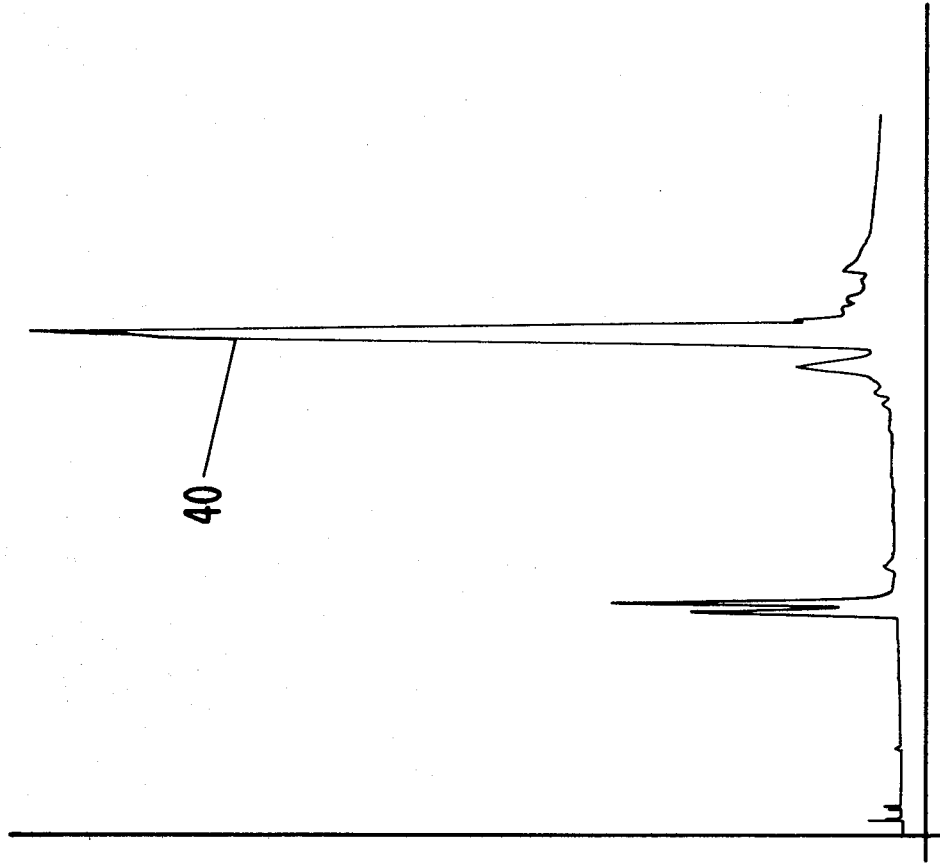
Figure 4:
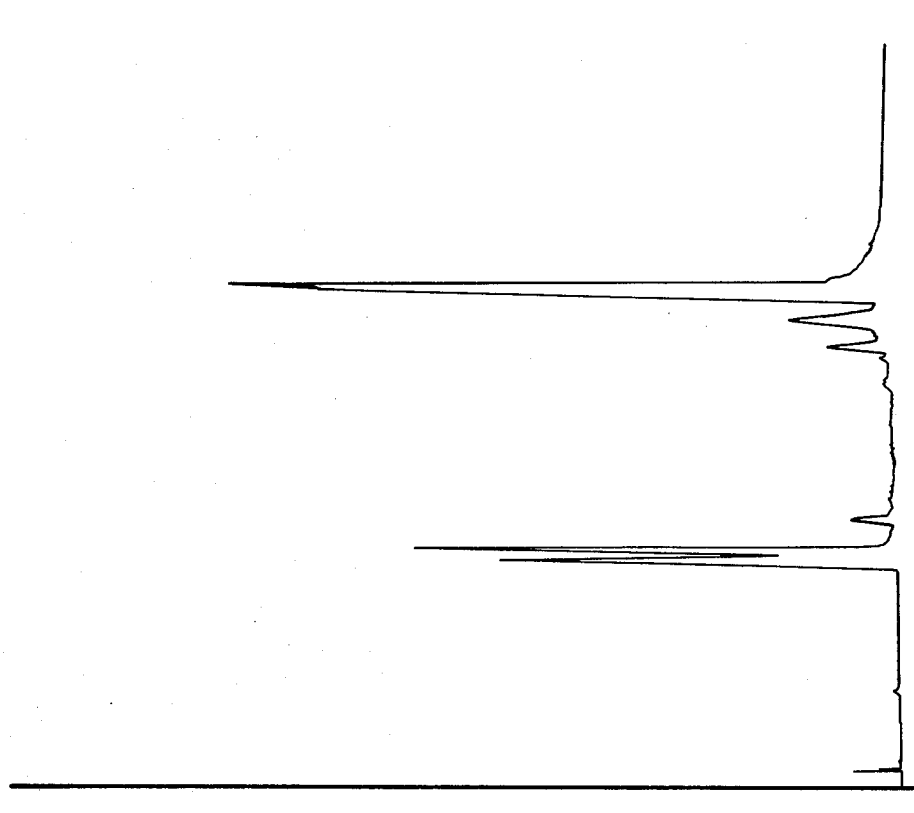

FIG. 3 is the GLC profile for fraction 1 of the first distillation of the reaction product of Example II containing the compounds defined according to the structure:

FIG. 4 is the GLC profile for fraction 2 of the first distillation of the reaction product of Example II containing the compounds defined according to the structure:

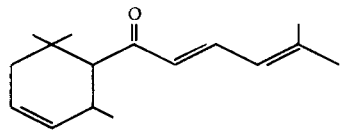

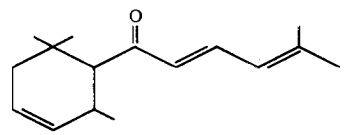

Figure 5:
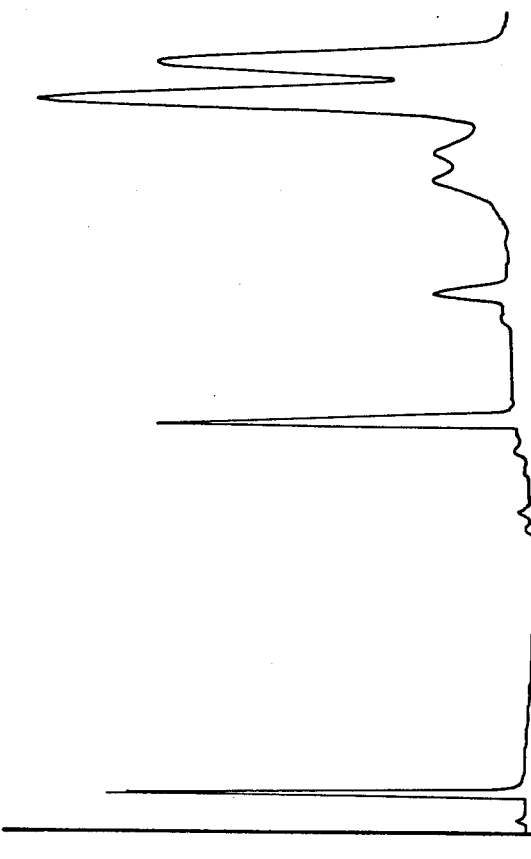

FIG. 5 is the GLC profile for fraction 4 of the re-distillation of the reaction product of Example II containing the compounds having the structure:

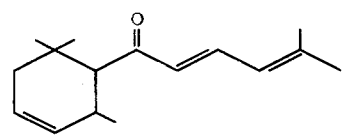

Figure 6:
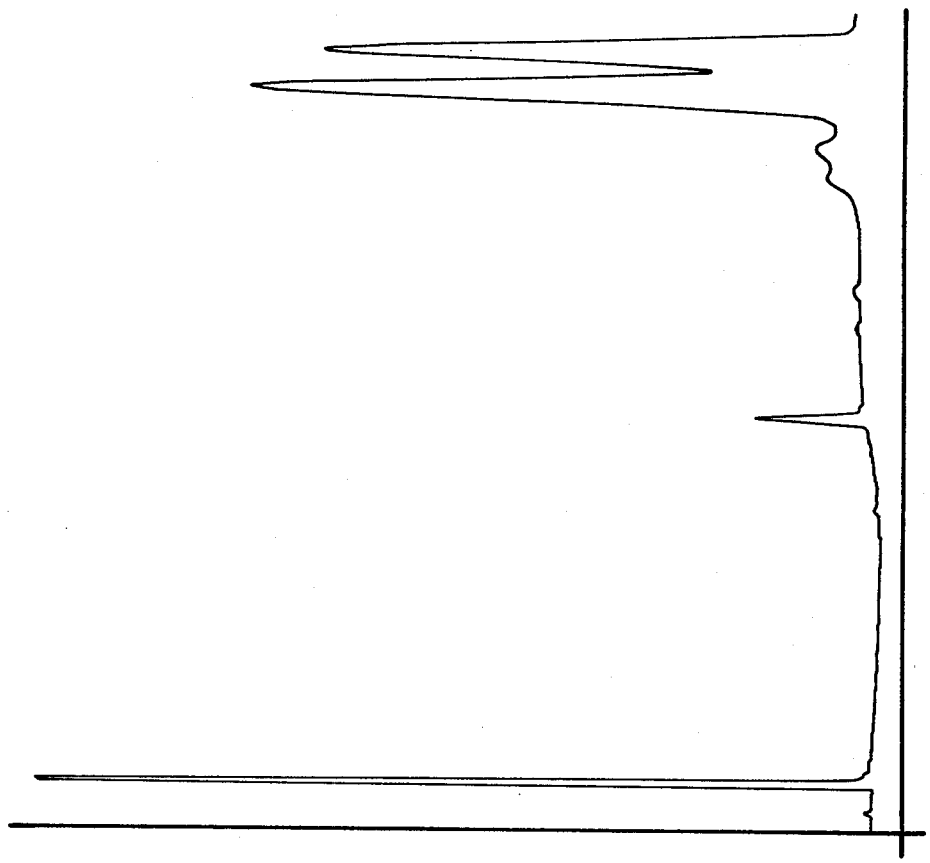

FIG. 6 is the GLC profile for fraction 5 of the re-distillation product of Example II containing the compound having the structure:

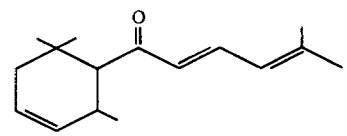

Figure 7:
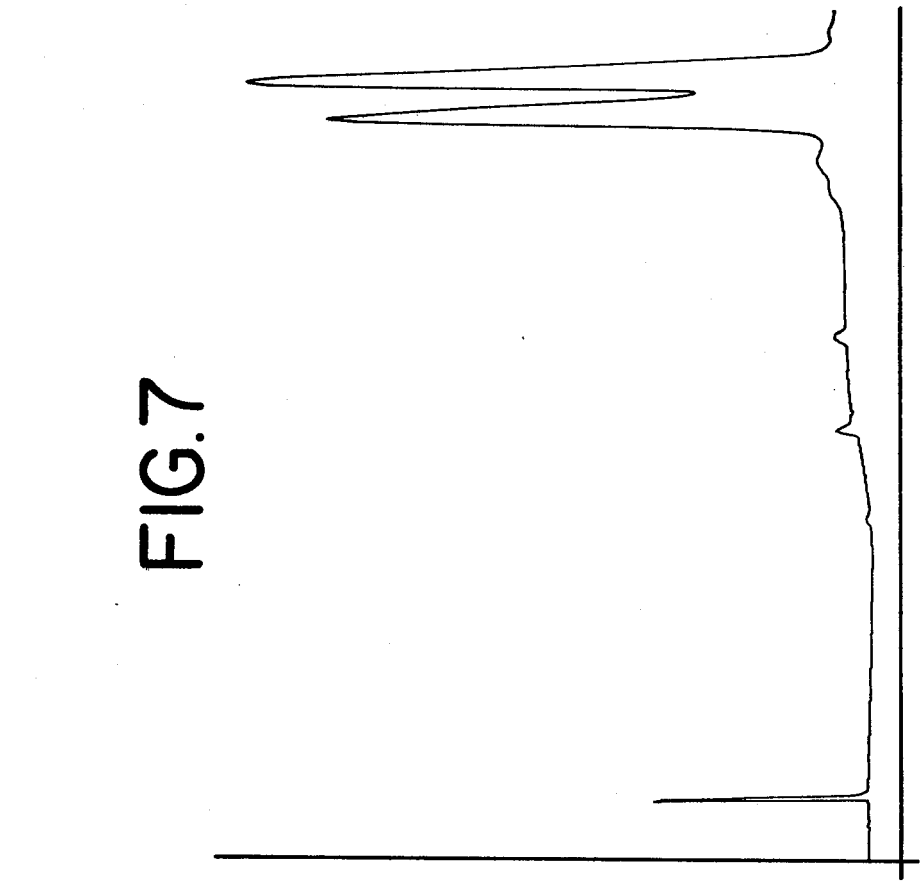

FIG. 7 is the GLC profile for fraction 6 of the re-distillation product of the reaction product of Example II containing the compounds having the structure:

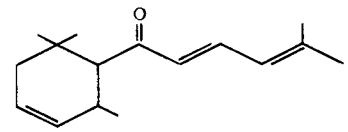

Figure 8:
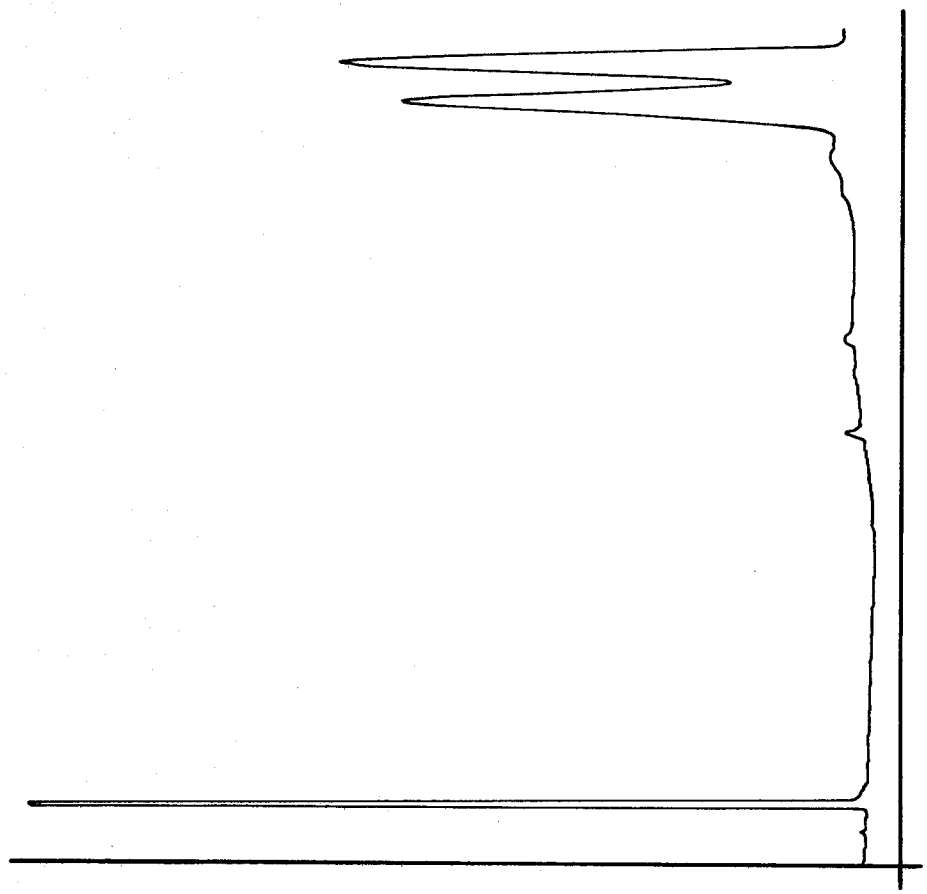

FIG. 8 is the GLC profile for fraction 7 of the re-distillation product of the reaction product of Example II containing the compounds having the structure:

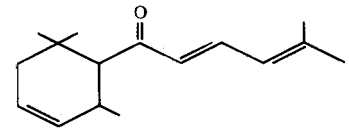

FIG. 9 is the NMR spectrum for the peak indicated by reference numeral "40" on the GLC profile of FIG. 4 containing the compound defined according to the structure:

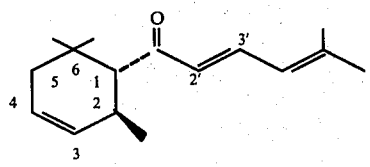

(the "Z, Z" isomer).

FIG. 10 is the infra-red spectrum for the peak indicated by reference numeral "40" on the GLC profile of FIG. 4 containing the compound having the structure:

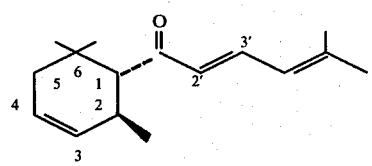

(the "Z, Z" isomer).

FIG. 11 is a partial side elevation and partial sectional view of an apparatus for forming scented polymer using the compounds defined according to the structure:

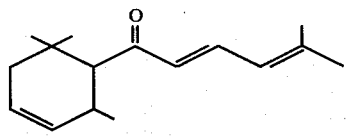

constructed in accordance with the invention.

FIG. 12 is a section taken on line 12—12 of FIG. 11.

DETAILED DESCRIPTION OF THE DRAWINGS

FIG. 4 is the GLC profile for fraction 2 of the first distillation of the reaction product of Example II containing the compounds defined according to the structure:

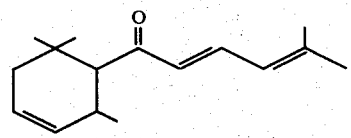

which include isomers having the structures:

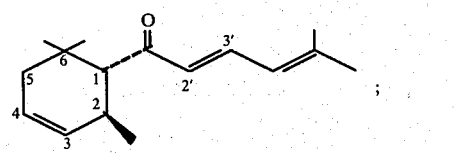

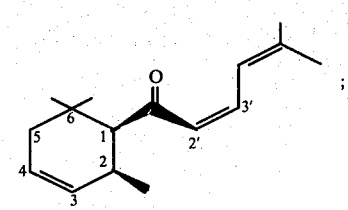

-continued

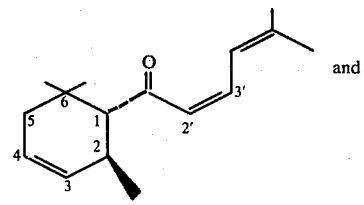

and

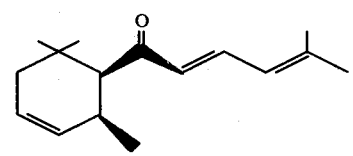

The peak indicated by reference numberal "40" is the peak for the compound which is the "Z, Z" isomer defined according to the structure:

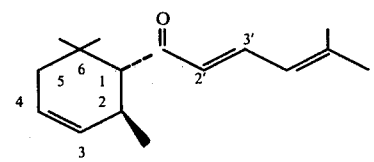

(conditions: SE-30 column programmed at 100°-220° C. at 8° C. per minute).

FIG. 9 is the NMR spectrum for the peak indicated by reference numeral "40" on FIG. 4 which is for the isomer defined according to the structure:

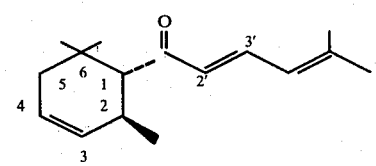

(the "Z, Z" isomer. Conditions: CFCl$_3$ solvent; 100 MHz field strength.)

Referring to the drawings in FIGS. 11 and 12 in particular, the invention embodied therein comprises a device for forming scented polymer pellets (e.g. polyethylene, polypropylene or mixtures of polyepsilon caprolactone and polyethylene or polypropylene or co-polymers of polyvinyl acetate and polyethylene) which comprises a vat or container into which a mixture of polymer such as polyethylene and the compound defined according to the structure:

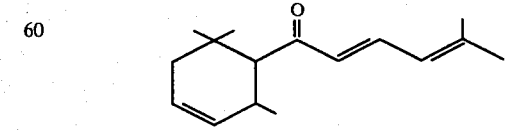

or a mixture of perfume materials including as a key ingredient one of the isomers defined according to the structure:

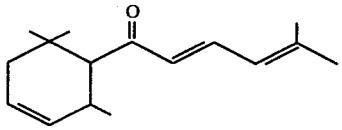

is placed.

The container is closed by an air-tight lid 228 clamped to the container by clamps 265. A stirrer 273 traverses the lid or cover 228 in air-tight manner and is rotated in suitable manner. A surrounding cylinder 212 having heating coils which are supplied with electrical current through cable 214 from a rheostat or control 216 is operated to maintain the temperature inside the container such that the polymer such as polyethylene in the container will be maintained in a molten or liquid state. It has been found advantageous to employ a colorless, odorless polymer such as low density polyethylene with a viscosity ranging between 180 and 220 centistokes and having a melting point in the neighborhood of 220° F. The heater 212A is operated to maintain the upper portion of the container within a temperature range of from 250°–350° F. An additional bottom heater 218 is regulated through a control 220 connected thereto through a connecting wire 222 to maintain the lower portion of the container within a temperature range of from 250° to 350° F.

In accordance with this aspect of the invention, a polymer such a polyethylene or polypropylene is added to the container and is then heated from 10 to 12 hours whereafter a scent or aroma imparting material containing the compound having the structure:

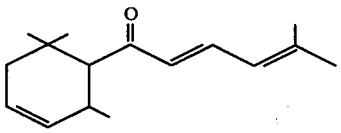

is quickly added to the melt. The material must be compatible with the polymer and forms a homogeneous liquid melt therewith. The heat resisting mixture generally about 10–40% by weight of material having the structure:

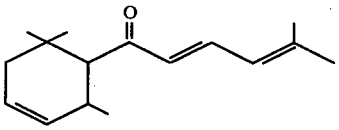

or mixture containing such compound or isomer is added to the polymer.

After the compound having the structure:

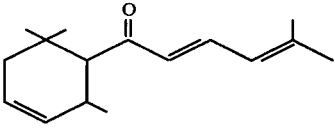

or mixture containing same is added to container, the mixture is stirred for a few minutes, for example 5 to 15 minutes, and maintained within the temperature range as indicated previously by the heating coils 212A and 218 respectively. The controls 216 and 220 are connected through cables 224 and 226 to a suitable supply of electric current for supplying the power for heating purposes.

Thereafter the valve "V" is opened permitting the mass to flow outwardly through a conduit 232 having a multiplicity of orifices 234 adjacent the lower side thereof. The outer end of the conduit 232 is closed so that the liquid polymer and substance containing compound having the structure:

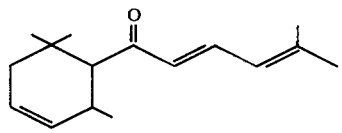

will continuously drop through the orifice 234 downwardly from the conduit 232. During this time the temperature of the polymer and the compound having the structure:

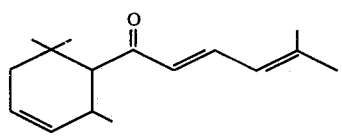

or mixture containing same in the container is accurately controlled so that a temperature in the range of from 210° F. up to 275° F. will exit in the conduit 232. The regulation of the temperature through the control 216 and the control 220 is essential in order to insure temperature balance to provide for the continuous dropping or dripping of molten polymer and material having the structure:

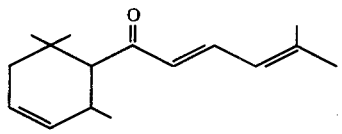

or mixture containing same through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 245 which is advantageously filled with water or some other suitable liquid to insure the rapid cooling of each of the pellets. The pellets 244 are then collected from the container 246 and packaged for shipment.

A feature of the invention is the provision for moistening the conveyor belt 238 to insure the rapid formation of the solid polymer scented pellets 244 without sticking to the belt. The belt 238 is advantageously of a material which will not normally stick to a melted polymer but the moistening means 248 insures a sufficiently cold temperature of the belt surface for the adequate formation of the pellets 244. The moistening means comprises a container 250 which is continuously fed with water to maintain a level for moistening a sponge element 256 which bears against the exterior surface of the belt 238.

THE INVENTION

The present invention provides the genus of compounds defined according to the structure:

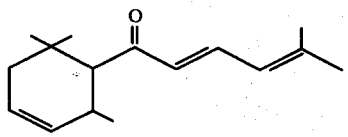

which include isomers defined according to the structures:

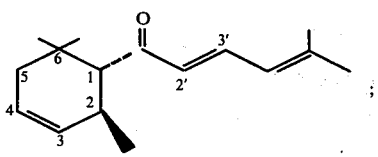

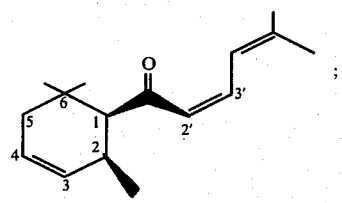

and

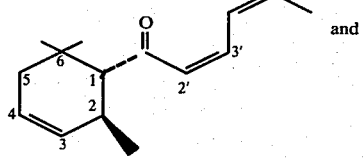

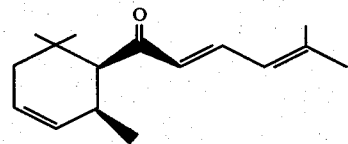

wherein the dashed line represents a "trans" configuration of the hexadienoyl moiety with respect to the monomethyl moiety bonded to the cyclohexene group, and a straight forward economical process directed towards synthesizing the compound defined according to the structure:

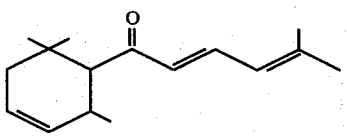

using the reaction sequence:

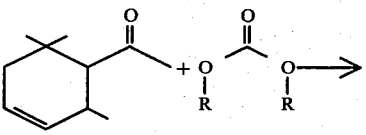

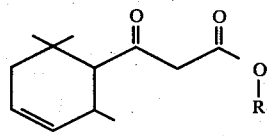

and

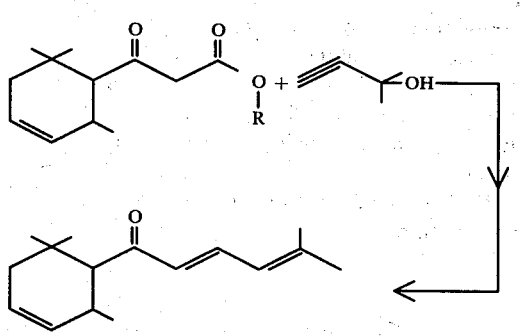

wherein R represents methyl or ethyl. Thus, the intermediate compounds defined according to the generic structure:

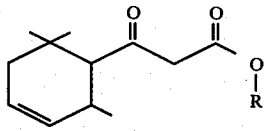

wherein R is methyl or ethyl and which include the isomers defined according to the structures:

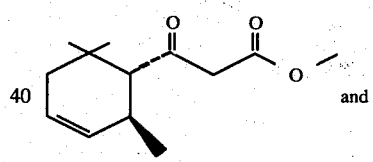

and

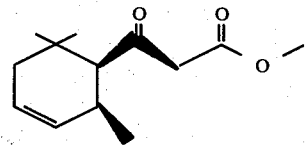

are novel compounds and are part of our invention.

Each of the members of the genus of compounds defined according to the structure:

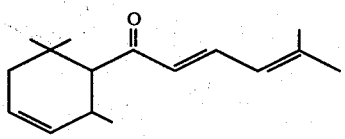

and the mixtures of such members of such genus are capable of augmenting or enhancing minty, citrus, lime, raspberry, floral and rosey aroma and taste nuances as well as imparting fresh, cooling nuances to lime, citrus, tropical fruit and mint flavors particularly in the oral hygiene area, e.g. mouthwashes and toothpastes and the like.

Each of the isomers of the genus having the structure:

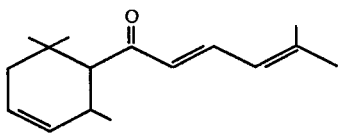

in addition, is capable of augmenting or enhancing floral, rosey, honey, woody and raspberry aroma nuances in perfume compositions, colognes and perfumed articles e.g. solid or liquid anionic, cationic, nonionic or zwitterionic detergents, fabric softener compositions, fabric softener articles, hair preparations and perfumed polymers.

Each of the members of the genus defined according to the structure:

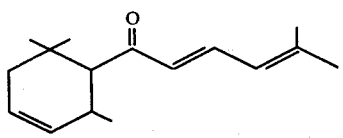

including the isomers thereof having the structures:

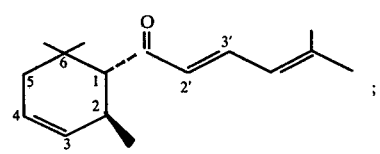

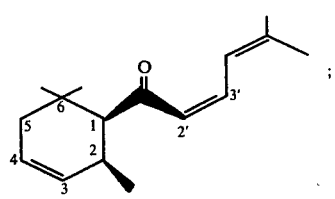

and

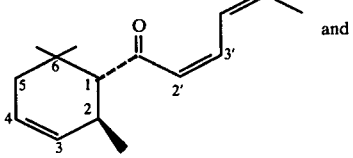

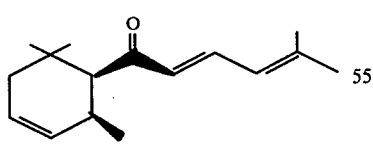

are capable of augmenting or enhancing the aroma and taste of smoking tobaccos and smoking tobacco articles wherein the floral, hay-like, sweet and fruity aroma and taste nuances both prior to and on smoking in the main stream and the side stream are augmented or enhanced. In addition, in the smoking tobacco articles and in the smoking tobacco per se, fresh, cooling nuances are imparted by the compounds defined according to the structure:

A genus of compounds defined according to the structure:

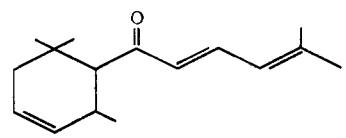

is prepared by a novel process of our invention embodied by the reaction sequence:

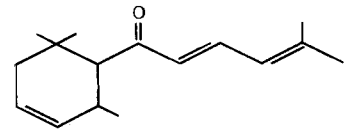

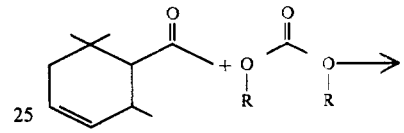

and

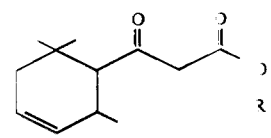

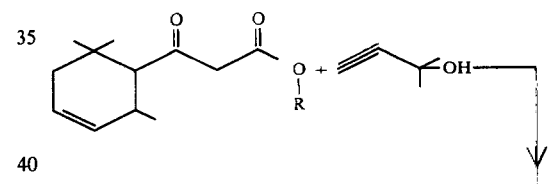

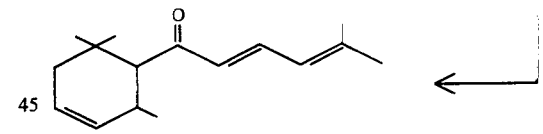

wherein R represents methyl or ethyl.

Thus, a mixture of compounds defined according to the genus:

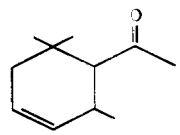

or individual isomers thereof having the structure:

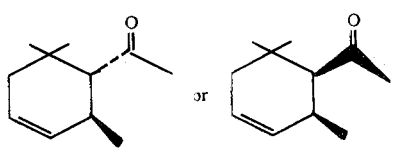

is reacted with a dialkyl carbonate defined according to the structure:

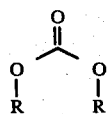

wherein R is methyl or ethyl using an alkali metal hydride in the presence of an inert solvent according to the reaction:

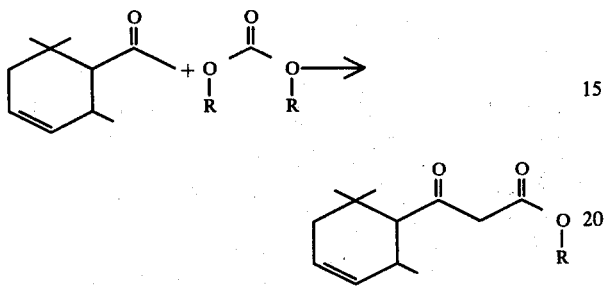

Examples of alkali metal hydride used are sodium hydride and potassium hydride. Examples of inert solvent (solvent inert to the reaction ingredients under the conditions of the reaction) are toluene, xylene, benzene and alkyl and polyalkyl substituted cyclohexane, e.g. 1,2,3,4,5,6-hexamethyl cyclohexane.

The reaction temperature is from about 30° C. up to about 80° C. The reaction pressure is from about 1 atmosphere up to about 10 atmospheres depending upon the desired reaction temperature and depending upon the particular solvent utilized. It is preferable to carry out the reaction under reflux conditions thereby minimizing the time of reaction and maximizing the yield.

The mole ratio of compound having the structure:

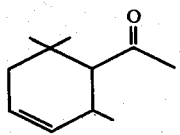

to dialkyl carbonate having the structure:

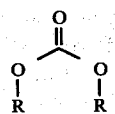

may vary from about 1:2 up to about 2:1 with a preferred mole ratio of about 1:1.5. The mole ratio of alkali metal hydride to compound having the structure:

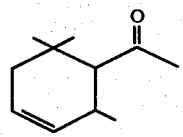

may vary from about 3:1 down to about 1:1 with a preferred mole ratio of about 2:1.

The concentration of alkali metal carbonate having the structure:

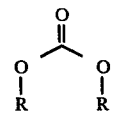

in the solvent may vary from about 1 mole per liter up to about 2 moles per liter with a concentration of about 1:5 moles per liter being preferable. The concentration of alkali metal hydride in the reaction mass may vary from about 1 mole per liter up to about 3 moles per liter with a concentration of about 1.8 moles per liter being preferred. The concentration of compound or isomer having the structure:

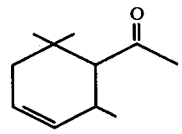

in the reaction mass may vary from about 0.5 moles per liter up to about 1.5 moles per liter with a concentration of about 0.9 moles per liter being preferred.

Since the isomer having the structure:

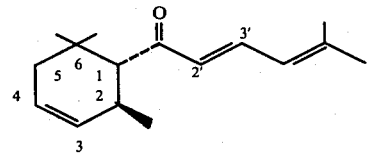

is the preferred isomer of our invention (although the other isomers are quite useful for their organoleptic properties), it is preferred to use as a starting material the isomer having the structure:

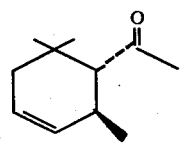

This isomer may be prepared by means of treatment of 1-alpha-acetyl-2-alpha,6,6-trimethyl-3-cyclohexene (prepared according to Ayyar, Cookson and Kagi, J. Chem. Soc., Perkin Trans. 1, 1975 (17) 1727–36 [title: "Synthesis of delta-Damascone[trans-1-(2,6,6-Trimethylcyclohex-3-enyl)but-2-en-1-one] and beta-Damascenone[trans-1-(2,6,6-Trimethylcyclohexa-1,3-dienyl)-but-2-en-1-one]") with refluxing alcoholic base or alkali metal alcoholate according to the reaction:

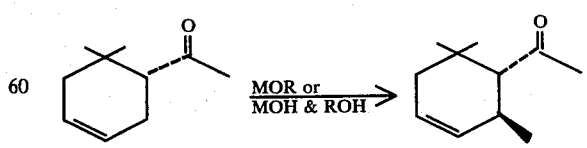

wherein R is lower alkyl, e.g. methyl or ethyl and M is alkali metal, e.g. sodium or potassium. From a practical standpoint, the resulting product contains a minor proportion of cis isomer (approximately 10–20%) and a major proportion of trans isomer (approximately 80–90%). Accordingly, the resulting material having the structure:

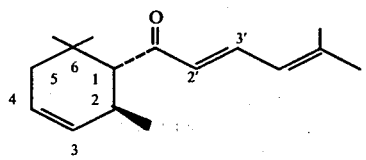

actually contains the additional isomers having the structures:

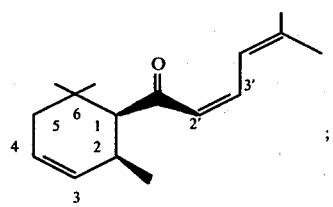

and

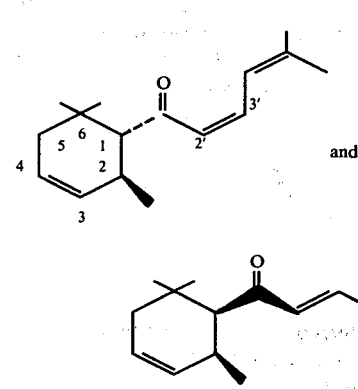

but from a practical standpoint, the amount of material having the structure:

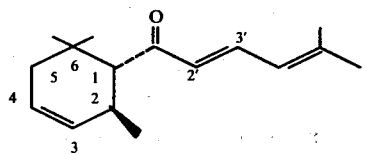

is about 80%.

The resulting product defined according to the structure:

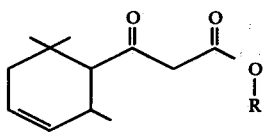

and containing the isomers having the structures:

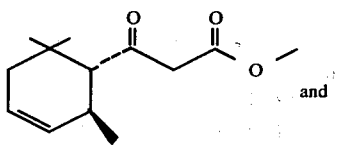

and

-continued

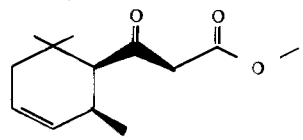

is then reacted with 2-methyl-3-butyn-2-ol having the structure:

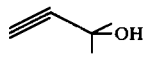

in the presence of a metal alkoxide, for example, sodium methoxide, potassium methoxide, sodium ethoxide, potassium ethoxide, potassium isobutoxide, potassium-t-butoxide and aluminum isopropoxide. The alkali metal alkoxide in this reaction is a catalytic quantity.

The reaction:

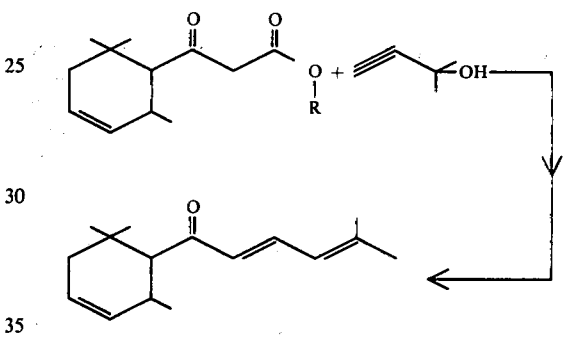

wherein R is methyl or ethyl, is carried out at a temperature of between about 70° C. and 200° C. While the reaction takes place, methane and carbon dioxide is devolved. The mole ratio of ester having the structure:

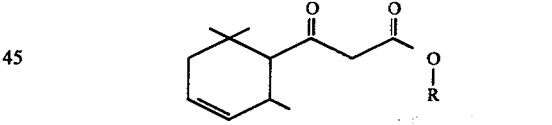

to 2-methyl-3-butyn-2-ol is from about 0.25:1 up to about 1:1 with a preferred mole ratio range of from about 0.3:1 up to about 0.5:1. The weight percent of metal alkoxide in the reaction mass is from about 5% up to about 20% with a preferred weight percent of metal alkoxide of about 8–10%.

At the end of the reaction, the reaction mass is quenched into a weak acid, e.g. acetic acid. The resulting material is extracted, for example, with toluene and the extracts are then stripped of solvent and fractionally distilled to yield the resulting product defined according to the structure:

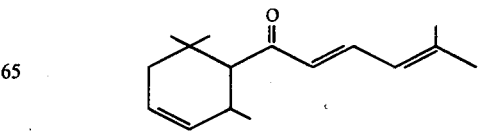

either as a mixture or as one of the isomers defined according to one of the structures:

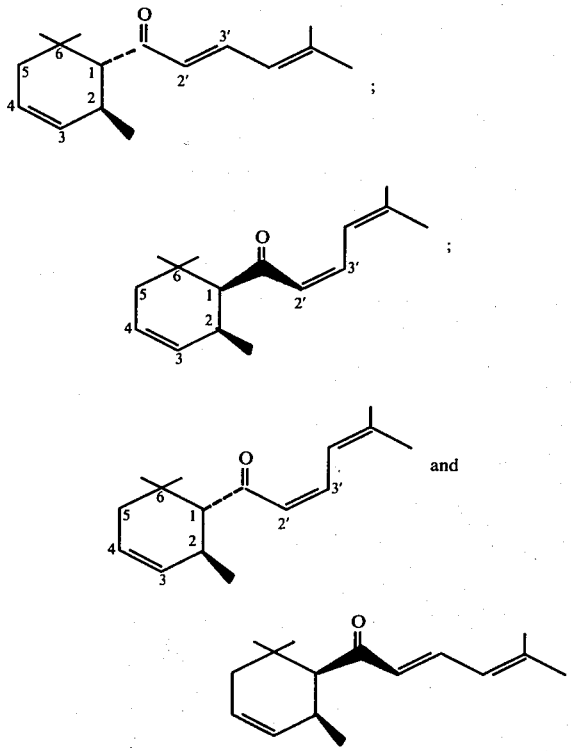

When the hexadienoyl cyclohexene derivatives of our invention are used as food flavor adjuvants, the nature of the co-ingredients included with the hexadienoyl cyclohexene derivatives used in formulating the product composition will also serve to alter, modify, augment or enhance the organoleptic characteristics of the ultimate foodstuff, chewing gum, toothpaste, medicinal product or chewing tobacco treated therewith.

As used herein in regard to flavors, the terms "alter", "modify" and "augment" in their various forms means supplying or imparting flavor character or note to otherwise bland, relatively tastless substances or augmenting the existing flavor characteristic where a natural flavor is deficient in some regard or supplementing the existing flavor impression to modify its quality, character or taste.

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle or substitute therefor, including jelutong, guttakay, rubber or certain comestible natural or synthetic resins or waxes. Incorporated with the gum base in admixture therewith may be plasticizers or softening agents, e.g. glycerine; and a flavoring composition which incorporates the hexadienoyl cyclohexene derivatives of our invention and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g. calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethylacrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e. foodstuff, whether simulated or natural, and should, in any event, (i) be organoleptically compatible with the hexadienoyl cyclohexene derivatives of our invention by not covering or spoiling the organoleptic properties (aroma and/or taste) thereof; (ii) be non-reactive with the hexadienoyl cyclohexene derivatives of our invention and (iii) be capable of providing an environment in which the hexadienoyl cyclohexene derivatives of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the hexadienoyl cyclohexene derivatives employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the hexadienoyl cyclohexene derivatives of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of the hexadienoyl cyclohexene derivatives of our invention ranging from a small but effective amount, e.g. 0.2 parts per million up to about 100 parts per million based on total composition are suitable. Concentrations in excess of the maximum quantity stated are not normally recommended, since they fail to provide commensurate enhancement of organoleptic properties. In those instances wherein the hexadienoyl cyclohexene derivatives of our invention are added to the foodstuff as an integral component of a flavoring composition, it is, of course, essential that the total quantity of flavoring composition employed be sufficient to yield an effective concentration of the hexadienoyl cyclohexene derivatives of our invention in the foodstuff product.

Food flavoring compositions prepared in accordance with the present invention preferably contain the hexadienoyl cyclohexene derivatives of our invention in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the hexadienoyl cyclohexene derivatives of our invention with, for example, gum arabic, gum tragacanth, carrageenan and the like, and thereafter spray-drying the resultant mixture whereby to obtain the particular solid product. Pre-prepared flavor mixes in powder form, e.g. a fruit flavored powder mix, are obtained by mixing the dried solid components, e.g. starch, sugar and the like, and the hexadienoyl cyclohexene derivatives of our invention in a dry blender until the requisite degree of uniformity is achieved.

It is presently preferred to combine with the hexadienoyl cyclohexene derivatives of our invention the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
β-Damascone (1-crotonyl-2,2,6-trimethylcyclohex-1-ene);
β-Damascenone (1-crotonyl-2,2,6-trimethylcyclohexa-1,3-diene);
Beta-cyclohomocitral (2,2,6-trimethylcyclohex-1-ene carboxaldehyde);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl) norbornadiene The hexadienoyl cyclohexene derivatives of our invention and one or more auxiliary perfume ingredients, including for example, alcohols, aldehydes, ketones other than the hexadienoyl cyclohexene derivatives of our invention, terpinic hydrocarbons, nitriles, esters, lactones, natural essential oils and synthetic essential oils, may be admixed so that the combined odors of the individual components produce a pleasant and desired fragrance, particularly and preferably in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, it is the individual components which contribute to their particular olfactory characteristics, however, the overall sensory effect of the perfume composition will be at least the sum total of the effects of each of the ingredients. Thus, the hexadienoyl cyclohexene derivatives of our invention can be used to alter, modify or enhance the aroma characteristics of a perfume composition, for example, by utilizing or moderating the olfactory reaction contributed by another ingredient in the composition.

The amount of hexadienoyl cyclohexene derivatives of our invention which will be effective in perfume compositions as well as in perfumed articles and colognes depends on many factors, including the other ingredients, their amounts and the effects which are desired. It has been found that perfume compositions containing as little as 0.01% of the hexadienoyl cyclohexene derivatives of our invention or even less (e.g. 0.005%) can be used to impart floral, rosey, honey, woody and raspberry note to soaps, cosmetics and other products. The amount employed can range up to 70% of the fragrance components and will depend on considerations of cost, nature of the end product, the effect desired in the finished product and the particular fragrance sought.

The hexadienoyl cyclohexene derivatives of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens, powders such as talcs, dusting powders, face powders and the like. When used as (an) olfactory component(s) as little as 1% of the hexadienoyl cyclohexene of our invention will suffice to impart an intense floral note to rose formulations. Generally no more than 3% of the hexadienoyl cyclohexene derivatives of our invention based on the ultimate end product is required in the perfume composition.

In addition, the perfume composition or fragrance composition of our invention can contain a vehicle or carrier for the hexadienoyl cyclohexene derivatives of our invention. The vehicle can be a liquid such as an alcohol, a non-toxic glycol or the like. The carrier can also be an absorbent solid such as a gum (e.g. gum arabic) or components for encapsulating the composition (such as gelatin).

The hexadienoyl cyclohexene derivatives of our invention may be blended into polymers when forming a perfumed polymer by means of extrusion using a single or double screw extruder or technique such as that set forth in U.S. Pat. No. 4,247,498 issued on Jan. 27, 1981 which discloses microporous polymers which are capable of containing volatile substances such as perfumes and the like and forms ranging from films to blocks and intricate shapes from synthetic thermoplastic polymers such as olefinic condensation or oxidation polymers. The specification of U.S. Pat. No. 4,247,498 is incorporated by reference herein. Other techniques of blending the hexadienoyl cyclohexene derivatives of our invention with polymers are exemplified in U.S. Pat. No. 3,505,432 (the specification for which is incorporated by reference herein) which discloses a method for scenting a polyolefin with such materials as the hexadienoyl cyclohexene derivatives of our invention which comprises:

(a) mixing a first amount of the liquid polyolefin (e.g. polyethylene or polypropylene) with a relatively large amount of scent-imparting material (in this case the hexadienoyl cyclohexene derivatives of our invention) to form a flowable mass;

(b) forming drops of said mass and causing substantially instantaneous solidification of said drops into polyolefin pellets having a relatively large amount of such scent-imparting materials as the hexadienoyl cyclohexene derivatives of our invention imprisoned therein;

(c) melting said pellets with a second amount of polyolefin and said second amount being larger than the first amount; and (d) solidifying the melt of (c).

Furthermore, the hexadienoyl cyclohexene derivatives of our invention are capable of supplying and/or potentiating certain flavor and aroma notes usually lacking in many tobacco flavors heretofore provided.

As used herein in regard to tobacco flavors, the terms "alter" and "modify" in their various forms means supplying or imparting flavor character or note to otherwise bland tobacco, tobacco substitutes, or tobacco flavor formulations or augmenting the existing flavor characteristic where a natural flavor is deficient in some regard or supplementing the existing flavor impression to modify its quality, character or taste.

As used herein, the term "enhance" is intended to mean the intensification (without change in kind or quality of aroma or taste) of one or more taste and/or aroma nuances present in the organoleptic impression of tobacco or a tobacco substitute or a tobacco flavor.

Our invention thus provides an organoleptically improved smoking tobacco product and additives therefor, as well as methods of making the same which overcome specific problems heretofore encountered in which specific desired floral, hay-like, sweet and fruity aroma and taste nuances thereof are created or enhanced and may be readily controlled and maintained at the desired uniform level regardless of variations in the tobacco components of the blend.

This invention further provides improved tobacco additives and methods whereby various floral, hay-like, sweet and fruity notes may be imparted to smoking tobacco products and may be readily varied and controlled to produce the desired uniform flavor characteristics.

In carrying out this aspect of our invention, we add to smoking tobacco materials or a suitable substitute therefor (e.g. dried lettuce leaves) an aroma and flavor additive containing as an active ingredient at least one of the hexadienoyl cyclohexene derivatives of our invention.

In addition to the hexadienoyl cyclohexene derivatives of our invention, other flavoring and aroma additives may be added to the smoking tobacco materials or substitute therefor either separately or in admixture with the hexadienoyl cyclohexene derivatives of our invention as follows:

(i) Synthetic Materials

Beta-ethyl-cinnamaldehyde;
Beta-cyclohomocitral;
Eugenol;
Dipentene;
Damascenone;
Damascone;
Maltol;
Ethyl Maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho[-2,1b]-furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils

Celery seed Oil;
Coffee extract;
Bergamot Oil;
Cocoa extract;
Nutmeg Oil;
Origanum Oil.

An aroma and flavoring concentrate containing the hexadienoyl cyclohexene derivatives of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g. dried lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of the hexadienoyl cyclohexene derivatives of our invention to smoking tobacco material is between 250 ppm and 1,500 ppm (0.025%–0.15%) of the active ingredients to the smoking tobacco material. We have further found that satisfactory results are obtained if the proportion by weight of the sum total of the hexadienoyl cyclohexene derivatives of our invention used to flavoring material is between 2,500 and 15,000 ppm (0.25%–1.5%).

Any convenient method for incorporating the hexadienoyl cyclohexene derivatives of our invention in the tobacco product may be employed. Thus, the hexadienoyl cyclohexene derivatives of our invention taken alone or along with other flavoring additives may be dissolved in a suitable solvent such as ethanol, pentane, diethylether and/or other volatile organic solvents and the resulting solution may either be sprayed on the cured, cased and blended tobacco material or the tobacco material may be dipped into such solution. Under certain circumstances, a solution of the hexadienoyl cyclohexene derivatives of our invention taken alone or further together with other flavoring additives as set forth above may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the hexadienoyl cyclohexene derivatives of our invention in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of the compound defined according to the structure:

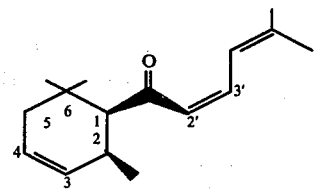

in an amount to provide a tobacco composition containing 800 ppm by weight of the compound having the structure:

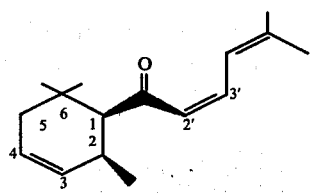

Thereafter the alcohol is removed by evaporation and the tobacco is manufactured into cigarettes by the usual techniques. The cigarette, when treated as indicated, has a desired and pleasing aroma (increased smoke body sensation in the mouth with enhanced tobacco-like notes and pleasant aromatic nuances) which is detectable in the main and side streams when the cigarette is smoked. This aroma is described as having floral, hay-like, sweet and fruity notes.

While our invention is particularly useful in the manufacture of smoking tobacco, such as cigarette tobacco, cigar tobacco and pipe tobacco, other tobacco products formed from sheeted tobacco dust or fines may also be used. Likewise, the hexadienoyl cyclohexene derivatives of our invention can be incorporated with materials such as filter tip materials, seam paste, packaging materials and the like which are used along with tobacco to form a product adapted for smoking. Furthermore, the hexadienoyl cyclohexene derivatives of our invention can be added to certain tobacco substitutes of natural or synthetic origin (e.g. dried lettuce leaves) and, accordingly, by the term "tobacco" as used throughout this specification is meant any composition intended for human consumption by smoking or otherwise, whether composed of tobacco plant parts or substitute materials or both.

The following Examples I and II serve to illustrate methods for preparing the hexadienoyl cyclohexene derivatives of our invention. The following Examples III et seq. serve to illustrate methods of utilizing the hexadienoyl cyclohexene derivatives of our invention for their orgnaoleptic properties.

All parts and percentages given herein are by weight unless otherwise specified.

EXAMPLE I

PREPARATION OF THE METHYL ESTER OF 3-KETO-3-(2'2'6'-TRIMETHYL Δ$^4$ CYCLOHEXENYL) PROPANIC ACID

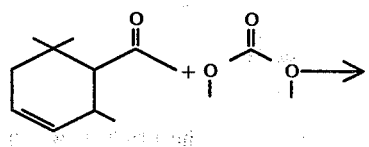

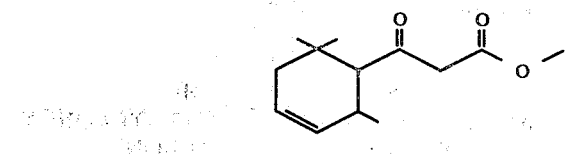

Into a 3 liter reaction flask equipped with stirrer, condenser, thermometer and dropping funnel and a nitrogen blanket apparatus is placed 1,000 cc of toluene. Dropwise over a period of 30 minutes, 90 grams (2.0 moles) of a 50% sodium hydride (in toluene) solution is added. Over a period of 1 hour while maintaining the temperature at 50° C., 135.0 grams (1.5 moles) of dimethyl carbonate is added. While maintaining the reaction mass at 50° C., in order to initiate the reaction, 2 cc of methyl alcohol and 5 grams of ALIQUAT®336 (trimethyl capryl ammonium chloride manufactured by the Henkel Chemical Company of Minneopolis Minn.) is added. The reaction mass is heated to 80° C. and dropwise over a period of 1 hour, the compound having the structure:

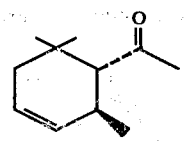

is added to the reaction mass. After the addition, the reaction mass is continued to be heated at 80° C. for a period of 3.5 hours. The excess sodium hydride is then decomposed with 200 cc of a 50:50 mixture of acetic acid and water.

The organic layer is separated from the aqueous phase and the organic phase is then washed with two 200 cc portions of water followed by two 200 cc portions of saturated sodium bicarbonate solution and one 200 cc portion of saturated sodium chloride solution.

The solvent is stripped and the reaction mass is distilled on a 12" stone packed column yielding the following fractions:

| Fraction Number | Vapor Temp. (°C.) | Liquid Temp. (°C.) | Vacuum mm/Hg. |
|---|---|---|---|
| 1 | 65/70 | 115/120 | 6.5/6.5 |
| 2 | 110 | 125 | 6.5 |
| 3 | 122 | 130 | 6.5 |
| 4 | 127 | 141 | 6.5 |
| 5 | 128 | 181 | 6.5 |
| 6 | 165 | 225 | 6.5 |

NMR, IR and mass spectral analyses yield the information that the resulting product has the structure:

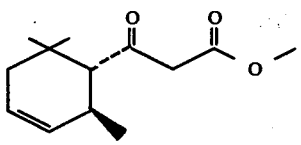

(primarily).

Figure 1:
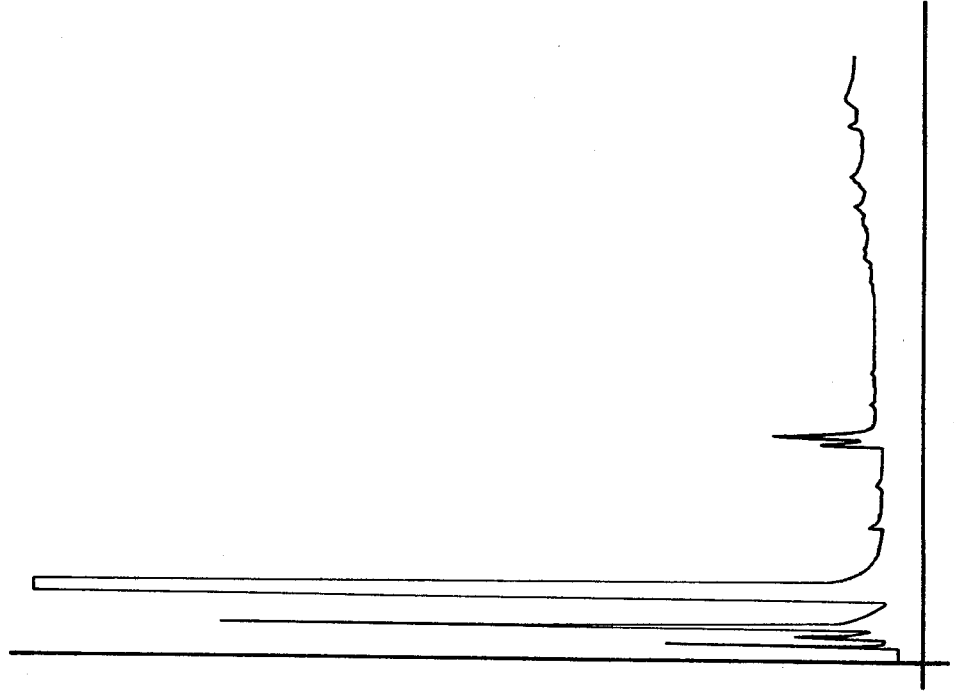
FIG. 1 is the GLC profile for the crude reaction product of Example I containing the compounds defined according to the structure.

FIG. 1 is the GLC profile for the crude reaction product prior to distillation.

EXAMPLE II

PREPARATION OF 5-METHYL-1-(2,6,6-TRIMETHYL-3-CYCLOHEXEN-1-YL)-2,4-HEXEDIEN-1-ONE

Reaction:

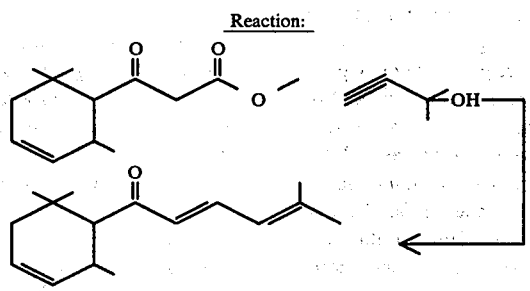

Into a 1 liter reaction flask equipped with a 12" Goodloe column and fractionation head is placed the following ingredients:

112.0 grams (0.5 moles) of the ester prepared according to Example I having the structure:

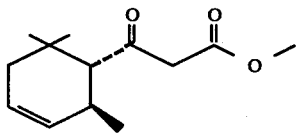

(primarily) with a minor proportion of the compound having the structure:

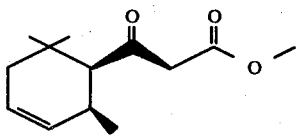

111.0 grams (1.32 moles) of 2-methyl-3-butyn-2-ol having the structure:

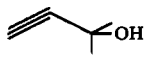

20.0 grams of aluminum isopropoxide.

The resulting mixture with stirring is heated to 80°–180° C. During the reaction methane and carbon dioxide reaction products are distilled off.

When both the methane and the carbon dioxide cease to be evolved, the reaction mass is then quenched into a 50:50 mixture of acetic acid and water.

The reaction mass is then extracted with two 100 cc portions of toluene. The toluene extracts was washed as follows:

(i) one 200 cc portion of water;
(ii) one 200 cc portion of saturated sodium bicarbonate;
(iii) one 200 cc portion of saturated sodium chloride solution.

The resulting product is then stripped of solvent and distilled on a 12" stone packed column yielding the following two fractions:

| Fraction Number | Vapor Temp. (°C.) | Liquid Temp. (°C.) | Vacuum mm/Hg. |
|---|---|---|---|
| 1 | 128 | 195 | 1.4 |
| 2 | 135 | 260 | 1.2 |

The resulting two products are bulked and redistilled on a spinning band column yielding the following fractions:

| Fraction Number | Vapor Temp. (°C.) | Liquid Temp. (°C.) | Vacuum mm/Hg | Weight of Fraction (grams) |
|---|---|---|---|---|
| 1 | 30/40 | 80/80 | 0.8/0.8 | 1.0 |
| 2 | 45 | 80 | 0.8 | 2.8 |
| 3 | 48 | 150 | 1.0 | 2.8 |
| 4 | 85 | 158 | 1.0 | 5.0 |
| 5 | 90 | 168 | 1.0 | 5.8 |
| 6 | 96 | 200 | 1.0 | 6.0 |
| 7 | 40 | 230 | 1.0 | 3.5 |

GLC, NMR, IR and mass spectral analyses yield the information that the resulting product is primarily a compound having the structure:

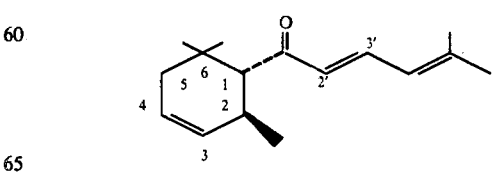

with minor amounts of compounds having the structures:

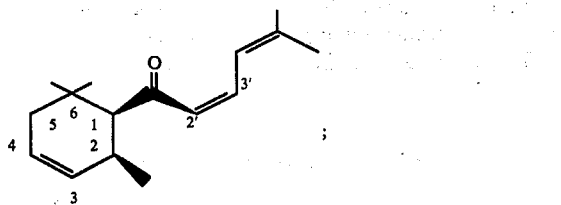

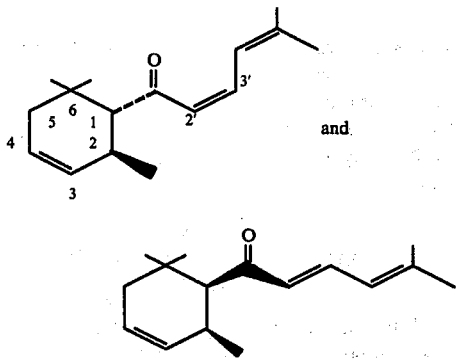

and

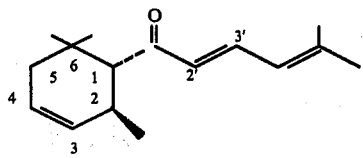

FIG. 2 is the GLC profile for the crude reaction product prior to the first distillation.

FIG. 3 is the GLC profile for fraction 1 of the first distillation (conditions: SE-30 column programmed at 100°–220° C. at 8° C. per minute).

FIG. 4 is the GLC profile for fraction 2 of the first distillation. The peak indicated by reference numeral "40" is the peak for the compound having the structure:

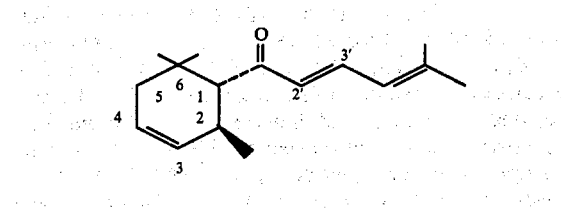

FIG. 5 is the GLC profile for fraction 4 of the second distillation product as set forth above (conditions: Carbowax column programmed at 100°–220° C. at 8° C. per minute).

FIG. 6 is the GLC profile for fraction 5 of the second distillation.

FIG. 7 is the GLC profile for fraction 6 of the second distillation.

FIG. 8 is the GLC profile for fraction 7 of the second distillation.

FIG. 9 is the NMR spectrum for the peak indicated by reference numeral "40" of fraction 2 of the first distillation, the reference numeral "40" being on FIG. 4 (conditions: 100 MHz field strength; CFCl$_3$ solvent).

FIG. 10 is the infra-red spectrum for the peak indicated by reference numeral "40" which is the peak for the compound having the structure:

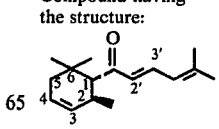

on the GLC profile of FIG. 4.

EXAMPLE III

COMPARISON OF PERFUME COMPOSITIONS CONTAINING ISOMERS OF MATERIALS PRODUCED ACCORDING TO EXAMPLE II

Isomers having the structures:

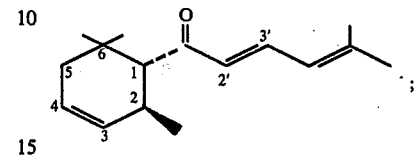

;

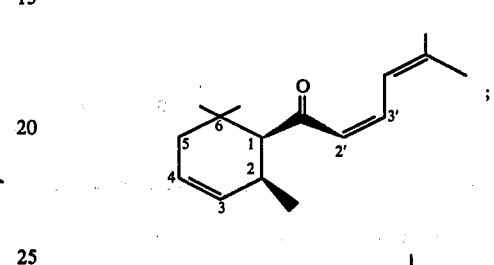

;

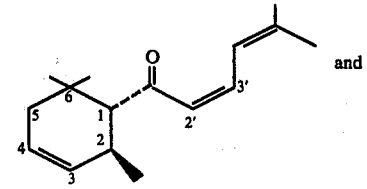

and

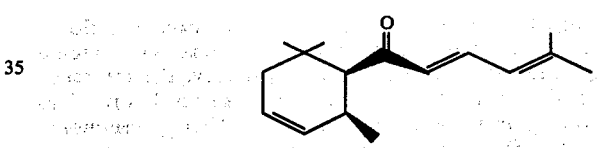

are compared side by side in a rose perfume which contains the following mixtures:

| Ingredients | Parts by Weight | | | |
| --- | --- | --- | --- | --- |
| | III (A) | III (B) | III (C) | III (D) |
| Rhodinol | 250 | 250 | 250 | 250 |
| Phenylethyl alcohol | 195 | 195 | 195 | 195 |
| Alpha methyl ionone | 80 | 80 | 80 | 80 |
| Linalyl acetate | 60 | 60 | 60 | 60 |
| Cis-3-hexenyl acetate | 5 | 5 | 5 | 5 |
| Jasmine absolute | 10 | 10 | 10 | 10 |
| Cinnamic alcohol | 20 | 20 | 20 | 20 |
| Rhodinyl acetate | 60 | 60 | 60 | 60 |
| Cyclohexyl ethyl alcohol | 20 | 20 | 20 | 20 |
| Geraniol | 130 | 130 | 130 | 130 |
| Geranyl acetate | 80 | 80 | 80 | 80 |
| Paraisopropyl cyclohexanol | 60 | 60 | 60 | 60 |
| Diethyl phthalate | 30 | 30 | 30 | 30 |
| Trans,trans-delta-damascone produced according to U.S. Letters Pat. No. 4,334,098, the specification for which is incorporated by reference herein | 30 | 30 | 30 | 30 |
| Compound having the structure: | 30 | 0 | 0 | 0 |

Compound having the structure:

| Ingredients | Parts by Weight | | | |
|---|---|---|---|---|
| | III (A) | III (B) | III (C) | III (D) |
| 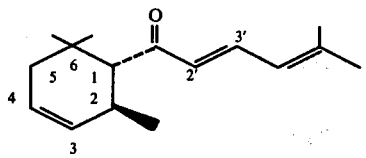 Compound having the structure: | 0 | 30 | 0 | 0 |
| 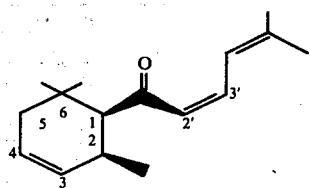 Compound having the structure: | 0 | 0 | 30 | 0 |
| 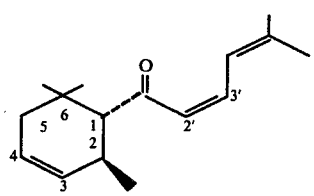 | 0 | 0 | 0 | 30 |

The compound having the structure:

imparts to this rose formulation an excellent floral, honey, woody, "raspberry"-like aroma with intense patchouli-like undertones. Accordingly, the fragrance produced using this formulation can be described as having an intense, rose aroma with honey, patchouli, raspberry-like undertones and apple, green and sweet topnotes.

The compound having the structure:

imparts to this rose formulation an excellent honey, woody, "mahogany-like" aroma. Accordingly, the resulting perfume formulation can be described as an intense rose aroma with "mahogany-like" woody and honey undertones and apple, green and sweet topnotes.

The compound having the structure:

imparts a honey, green, woody, fresh raspberry aroma to this rose formulation. Accordingly, the resulting perfume composition can be described as having an intense rose aroma with green, woody, honey and raspberry undertones and apple, green and sweet topnotes.

The compound having the structure:

imparts a vetiver-like, honey and white rose aroma profile to this intense rose formulation. Thus, the perfume composition of Example III(D) can be described as an intense rose aroma with white rose, vetiver-like and honey nuances and apple, green and sweet topnotes.

EXAMPLE IV

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| Compound having the structure: 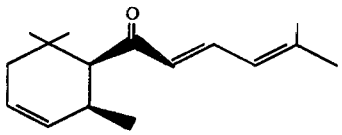 prepared according to Example II, bulked fractions 4–7. | An intense floral, rosey, honey, woody, raspberry-like aroma profile. |
| Perfume composition of Example III (A). | An intense, rose aroma with honey, patchouli, raspberry-like undertones and apple, green and sweet topnotes. |
| Perfume composition of Example III (B). | An intense rose aroma with "mahogany-like", woody and honey undertones and apple, green and sweet topnotes. |
| Perfume composition of Example III (C). | An intense rose aroma with green, woody, honey and raspberry undertones and apple, green and sweet topnotes. |
| Perfume composition of Example III (D). | An intense rose aroma with white rose, vetiver-like and honey nuances and apple, green and sweet topnotes. |

EXAMPLE V PERFUMED LIQUID DETERGENTS

Concentrated liquid detergents (lysine salt of n-dodecylbenzene sulfonic acid as more specifically described in U.S. Pat. No. 3,948,818, issued on Apr. 6, 1976 incorporated by reference herein) with aroma nuances as set forth in Table I of Example IV, are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

PREPARATION OF COLOGNES AND HANDKERCHIEF PERFUMES

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

PREPARATION OF SOAP COMPOSITIONS

One hundred grams of soap chips (per sample) (IVORY ® produced by the Proctor & Gamble Company of Cincinnati, Ohio), are each mixed with one gram samples of substances as set forth in Table I of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example IV.

EXAMPLE VIII

PREPARATION OF SOLID DETERGENT COMPOSITIONS

Detergents are prepared using the following ingredients according to Example 1 of Canadian Patent No. 1,007,948 (incorporated by reference herein):

| Ingredient | Percent by Weight |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example IV, supra.

EXAMPLE X

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example IV | 0.10 weight percent |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

CONDITIONING SHAMPOOS

Monamid CMA (prepared by the Mona Industries Company) (3.0 weight percent) is melted with 2.0 weight percent coconut fatty acid (prepared by Proctor & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat ®755 N polymer (manufactured by GAF Corporation of 140 West 51st Street, New York, N.Y.)

(5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

EXAMPLE XII

Scented polyethylene pellets having a pronounced scent as set forth in Table I of Example IV are prepared as follows:

75 pounds of polyethylene of a melting point of about 220° F. are heated to about 230° F. in a container of the kind illustrated in FIGS. 11 and 12. 25 pounds of each of the perfume materials of Table I of Example IV supra, are then added quickly to the liquified polyethylene. The lid 228 is put in place and the agitating means 273 are actuated. The temperature is maintained at about 225° F. and the mixing is then continued for about 5-15 minutes. The valve "V" is then opened to allow flow of the molten polyethylene enriched with each of the aroma substance-containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table I of Example IV supra are then formed. Analysis demonstrates that the pellets contain about 25% of each of the perfume substances of Table I of Example IV so that almost no losses of the scenting substance occur. These pellets may be called master pellets.

50 pounds of the scent-containing master pellets are then added to 1,000 pounds of unscented polyethylene powder and the mass is heated to the liquid state. The liquid is molded into thin sheets or films. The sheets or films have a pronounced aroma as set forth in Table I of Example IV supra. The sheets are also fabricated into garbage bags which have aromas as set forth in Table I of Example IV supra.

EXAMPLE XIII

TOBACCO FORMULATION

A tobacco mixture is prepared by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 1.0% to all of the cigarettes produced using the above tobacco formulation. Half of the cigarettes are then treated with 500 or 1,000 ppm of the product of Example II, bulked fractions 4-7 containing primarily the compound defined according to the structure:

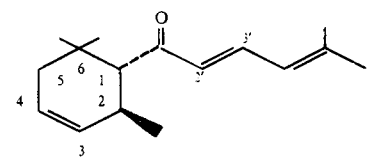

The control cigarettes not containing the compound having the structure:

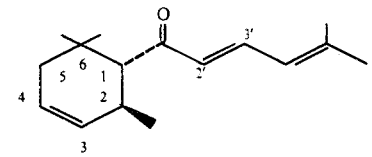

produced according to the process of Example II and the experimental cigarettes which contain the compound having the structure:

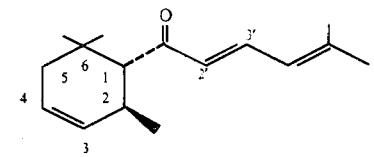

produced according to Example II are evaluated by paired comparison and the results are as follows:

The experimental cigarettes are found to have more body in tobacco smoke flavor and a fuller body sensation. The tobacco-like notes are enhanced and the flavor of the tobacco on smoking is more aromatic with floral, hay-like, sweet and fruity aroma and taste nuances.

The tobacco smoke flavors of the experimental cigarettes prior to smoking has floral, hay-tea-like, sweet and fruity notes.

All cigarettes are evaluated for smoke flavor with a 20 mm cellulose acetate filter.

EXAMPLE XIV

MANGO FLAVOR FORMULATION

Goya ® brand mango nectar (manufactured by Goya Foods Inc. of 25-12th Street, Brooklyn, N.Y.) is split into three samples.

To the first sample at the level of 3 ppm, the compound having the structure:

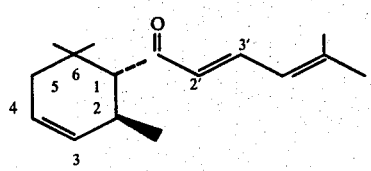

prepared according to Example II, bulked fractions 4–7 is added without anything else.

To the second sample, the following formulation is added:

| Ingredients | Parts by Weight |
|---|---|
| Compound having the structure: 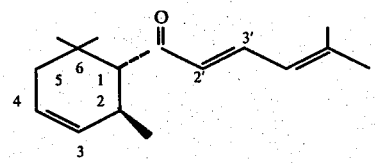 | 12.0 |
| Orange oil absolute | 8.0 |
| Lime oil absolute ex Mayaguez | 14.5 |
| Trans, trans-delta-damascone | 2.8 |
| Beta-damascone | 4.5 |
| 1-methyl-3-n-propyl-2,4-oxathiane | 12.4 | at the level of 12 ppm.

The mango nectar not containing any of the additional ingredients has a very bland taste. The mango nectar containing the additional compound having the structure:

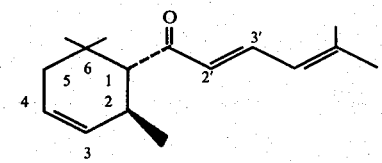

either taken alone or together with the other members of the formulation have minty, citrusy, lime, floral, rosey aroma and taste nuances in addition to fresh and cooling nuances.

EXAMPLE XV

TOOTHPASTE

At the level of 2 ppm, the compound having the structure:

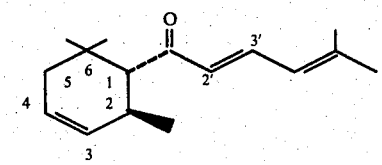

is added to a toothpaste formulation which has been previously unflavored (unflavored Crest ® manufactured by the Proctor & Gamble Company of Cincinnati, Ohio). The compound having the structure:

imparts a minty, citrusy, lime, floral and rosy taste with intense fresh, cooling nuances to the previously unflavored toothpaste.

A bench panel of 4 members (blind panel; employees of International Flavors & Fragrances Inc.) considered the formulation with the compound having the structure:

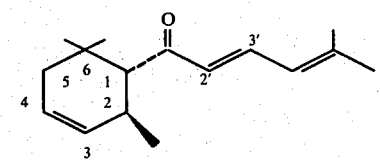

to be superior in taste to the formulation without the compound having the structure:

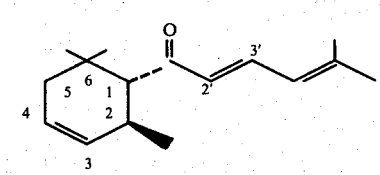

produced according to Example II.

Closely similar effects were obtained when using compounds having the structures:

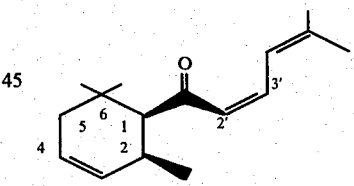

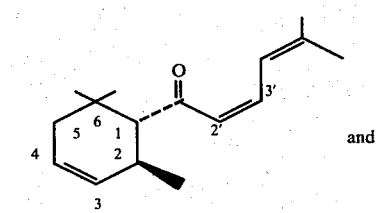

and

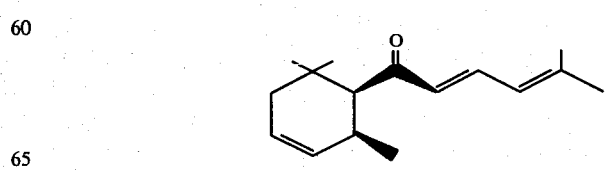

produced according to Example II by means of chromatographic separation.

EXAMPLE XVI

MOUTHWASH

To Scope® mouthwash (trademark of the Johnson & Johnson Company of New Brunswick, N.J.) at the level of 5 ppm, the compound having the structure:

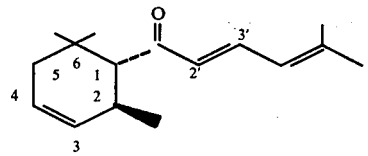

produced according to Example II is added. The compound having the structure:

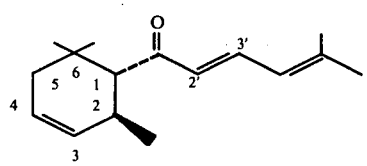

imparts to the Scope® mouthwash additional and pleasant minty, citrusy, lime and fresh, cooling nuances.

The resulting mouthwash is preferred by an independent blind bench panel of 4 members over the mouthwash without the compound having the structure:

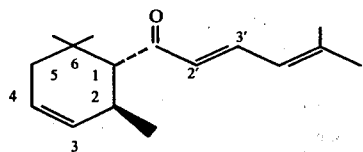

produced according to Example II.

What is claimed is:

1. A compound having the structure:

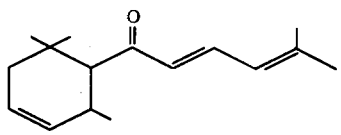

or an isomer thereof having a structure selected from the group consisting of:

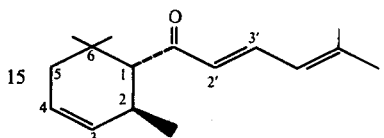

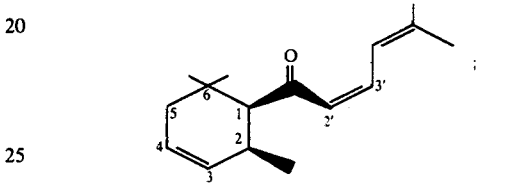

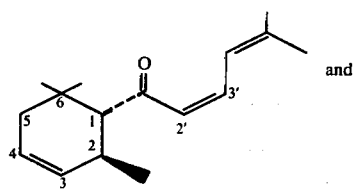

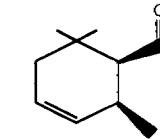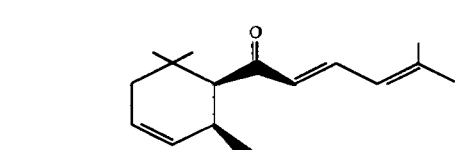 and

* * * * *